(12) United States Patent
Bayer et al.

(10) Patent No.: US 10,668,223 B2
(45) Date of Patent: Jun. 2, 2020

(54) DOSE INDICATING MECHANISM FOR A DRUG DELIVERY DEVICE

(71) Applicant: Sanofi, Paris (FR)

(72) Inventors: Stefan Bayer, Würselen (DE);
Wolfgang Pelzer, Kreuzau (DE);
Michael Pfoser, Kohlscheid (DE);
Björn Wilden, Simmerath (DE);
Philipp Zeitz, Aachen (DE)

(73) Assignee: Sanofi, Paris (FR)

( * ) Notice: Subject to any disclaimer, the term of this patent is extended or adjusted under 35 U.S.C. 154(b) by 693 days.

(21) Appl. No.: 14/916,834

(22) PCT Filed: Sep. 8, 2014

(86) PCT No.: PCT/EP2014/069037
§ 371 (c)(1),
(2) Date: Mar. 4, 2016

(87) PCT Pub. No.: WO2015/036346
PCT Pub. Date: Mar. 19, 2015

(65) Prior Publication Data
US 2016/0193425 A1    Jul. 7, 2016

(30) Foreign Application Priority Data

Sep. 10, 2013   (EP) .................................... 13183655

(51) Int. Cl.
*A61M 5/315*   (2006.01)
*A61M 5/20*    (2006.01)
*A61M 5/31*    (2006.01)

(52) U.S. Cl.
CPC .......... *A61M 5/31553* (2013.01); *A61M 5/20* (2013.01); *A61M 5/3157* (2013.01);
(Continued)

(58) Field of Classification Search
CPC ............ A61M 5/31553; A61M 5/3157; A61M 2005/3125; A61M 3005/3126;
(Continued)

(56) References Cited

U.S. PATENT DOCUMENTS

2009/0293870 A1* 12/2009 Brunnberg ........ A61M 5/31551
128/203.12
2011/0313365 A1    12/2011 Wieselblad
(Continued)

FOREIGN PATENT DOCUMENTS

| JP | 2012-528618 | 11/2012 |
| WO | WO 2010/139629 | 12/2010 |
| WO | WO2012/158138 | 11/2012 |

OTHER PUBLICATIONS

International Preliminary Report of Patentability and Written Opinion in International Application No. PCT/EP/2014/069037, dated Mar. 15, 2016, 7 pages.

(Continued)

*Primary Examiner* — Brandy S Lee
*Assistant Examiner* — Hong-Van N Trinh
(74) *Attorney, Agent, or Firm* — Fish & Richardson P.C.

(57) ABSTRACT

A dose indicating mechanism for a drug delivery device for displaying of a dose of a medicament to be dispensed by the drug delivery device includes an elongated housing extending in an axial direction and having at least a first window and a second window that are spaced apart from each other in axial direction. The dose indicating mechanism further includes a dose indicating sleeve movably disposed in the housing and having at least one dose indication coinciding with the first window to display the size of a dose actually set, and an indicator operably engaged with the dose indicating sleeve and axially displaceable relative to the housing (Continued)

to coincide with the second window for indicating an operational status of the dose indicating mechanism.

16 Claims, 11 Drawing Sheets

(52) U.S. Cl.
CPC ..... *A61M 5/31583* (2013.01); *A61M 5/31541* (2013.01); *A61M 2005/3125* (2013.01); *A61M 2005/3126* (2013.01); *A61M 2205/583* (2013.01); *A61M 2205/584* (2013.01)

(58) Field of Classification Search
CPC ...... A61M 5/31533; A61M 2005/3126; A61M 5/31525; A61M 5/31528; A61M 5/31535; A61M 5/31536; A61M 5/31538; A61M 2005/3154; A61M 5/31541; A61M 5/31543; A61M 5/31545; A61M 5/31548; A61M 5/3155; A61M 5/31551; A61M 5/3156; A61M 5/31561; A61M 5/31571; A61M 5/31568; A61M 5/31573; A61M 5/31578; A61M 5/3158; A61M 5/31581; A61M 5/31583; A61M 5/31585; A61M 5/31586; A61M 5/3159; A61M 5/31593
See application file for complete search history.

(56) References Cited

U.S. PATENT DOCUMENTS

2013/0016105 A1    1/2013   Raab et al.
2014/0046268 A1*   2/2014   Quinn ............... A61M 5/31541
                                                              604/209

OTHER PUBLICATIONS

International Search Report and Written Opinion in International Application No. PCT/EP2014/069037, dated Oct. 14, 2014, 9 pages.

* cited by examiner

A-A

B-B

C-C

D-D

DOSE INDICATING MECHANISM FOR A DRUG DELIVERY DEVICE

CROSS-REFERENCE TO RELATED APPLICATIONS

This application is a U.S. national stage application under 35 USC § 371 of International Application No. PCT/EP2014/069037, filed on Sep. 8, 2014, which claims priority to European Patent Application No. 13183655.3, filed on Sep. 10, 2013, the entire contents of which are incorporated herein by reference.

TECHNICAL FIELD

The present disclosure relates to a dose indicating mechanism for a drug delivery device and to a respective drug delivery device.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is typically provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

Drug delivery devices such like pen type injectors also provide a dose indicating mechanism which is operable to display the size of a dose actually set. Typically, the housing of such drug delivery devices comprises a dose indicating window in which an information content, in particular a number representing the size of the dose shows up.

Especially for elderly or impaired patients, reading of such dose indication or of does indicating numbers is sometimes difficult. Typically, the consecutive numbers illustrated by a dose indicating mechanism and representing the size of a dose actually set are also indicative of the actual operational status of the drug delivery device. For instance with injection devices such like pen-type injectors, the dose indicating mechanism may comprise a rotatable sleeve featuring a helical scale with consecutive numbers. During setting of a dose, such a dose indicating sleeve typically rotates in a dose incrementing direction, whereby the numbers displayed in a respective window of the device increment.

During a consecutive dose dispensing operation, the dose indicating sleeve typically revolves in an opposite sense of rotation, hence in a dose decrementing direction until it returns in initial configuration. Typically, in such an initial configuration a number like '0' may show up in the window thereby indicating, that the device is ready for setting and dispensing of a subsequent dose.

Many drug delivery devices further offer the possibility to interrupt a dose dispensing procedure. Respective drive mechanisms of such drug delivery devices may be sensitive to distally and externally applied dispensing forces that are to be exerted by the user of the device during the entire dose dispensing process. With many pen-type injectors, the user may simply have to depress an actuation member in distal direction, e.g. with a thumb. An early or premature release of the actuation member, i.e. before the dispensing process terminates, may immediately interrupt the dispensing and hence the injection procedure.

In such a situation the device is still operable to dispense a residual amount of the dose of the medicament previously set during a dose setting procedure. However, and due to the circumstances causing the patient to interrupt a dispensing procedure the patient or user may be simply unaware that dose dispensing has not terminated yet. In such circumstances there may persist a certain risk that the dose previously set is not completely dispensed and injected. Moreover, in a subsequent dose setting procedure, the user may be confused since dialing and setting of a dose may not start from an initial condition, in which a zero dose indicating number, such like '0' shows up in the dose indicating window.

SUMMARY

Certain aspects of the present invention relate to dose indicating mechanisms for a drug delivery device. In some aspects, a dose indicating mechanism can display the size of a dose actually set and can provide an additional safety feature to indicate to the patient or user that dose setting or dose dispensing is in progress and that the device is currently in use. The dose indicating mechanism can be further operable to unequivocally and to intuitively indicate to a user when the drug delivery device is in a standby mode starting from which a subsequent dose may be dialled or set. The drug delivery device can be, for example, a pen-type injector including a dose indicating window to visualize the size of a dose actually set.

Also, in certain aspects, the dose indicating mechanism is rather robust and provides the additional indicating functionality without implementing and arranging additional parts in the drug delivery device.

In certain aspects of the invention, a drive mechanism includes such a dose indicating mechanism. Moreover, in certain aspects of the invention, a drug delivery device engages with a cartridge or includes a cartridge sealed with a piston to become operably engaged with such drive mechanism.

In a first aspect a dose indicating mechanism for a drug delivery device is provided that is operable to display a dose of a medicament to be dispensed by said drug delivery device. The dose indicating mechanism comprises an elongated housing extending in an axial direction. Typically, the housing is of substantially tubular or cylindrical shape that allows gripping and operating of the drug delivery device and hence of the dose indicating mechanism by one hand of a user.

The elongated housing comprises at least a first window and a second window. First and second windows are spaced apart from each other at least in axial direction. Consequently, first and second windows of the housing are separated by some kind of housing portion. In this way, first and second windows can be clearly distinguished.

The dose indicating mechanism further comprises a dose indicating sleeve moveably disposed in the housing and having at least one dose indication coinciding with the first window to display the size of a dose actually set. The dose indication typically comprises a dose indicating scale or a dose indicating dial featuring consecutive numbers arranged in a predefined way on the outer circumference of the dose indicating sleeve. The respective dose indication is arranged and aligned on the outer circumference of the dose indicating sleeve in a way that directly corresponds to the movement of the dose indicating sleeve relative to the housing.

Additionally, the dose indicating mechanism also comprises an indicator that is operably engaged with the dose indicating sleeve. The indicator is further axially displaceable relative to the housing to coincide with the second window for indicating an operational status of the dose indicating mechanism, of the drug delivery device and/or of its drive mechanism. Typically, the indicator is operable to visualise at least one particular operational status of the dose indicating mechanism, of the drive mechanism and/or of the drug delivery device. For instance, the indicator may be operable to visually indicate that the dose indicating mechanism is in a zero dose configuration, in which the dose indicating mechanism and hence the drug delivery device and its drive mechanism is ready for a subsequent dose setting and dose dispensing procedure.

Typically, the dose indicating sleeve is moveable in the housing between a zero dose configuration representing a standby mode and a maximum dose configuration, in which a maximum size of a dose, e.g. 120 international Units (IU) of insulin have been set. In both end configurations, hence in the maximum dose configuration, in the zero dose configuration and also in any arbitrary position there between the dose indicating sleeve always covers or coincides with the first window.

In contrast to that, the indicator may only occasionally coincide with the second window to indicate at least one particular operational status of the dose indicating mechanism. The indicator may be particularly operable to indicate the standby mode of the device. As the dose indicating sleeve is subject to a movement during dose setting, the indicator may also become subject to a respective displacement, thereby moving beyond or outside the second window.

Hence, the indicator may comprise or provide a binary information content. It may either be present in the second window to visualise that the dose indicating mechanism is in standby mode. In all other configurations of the dose indicating mechanism, the indicator may not be visible in the second window. Instead, some other component of the dose indicating mechanism or of the drive mechanism may show up in the second window, thereby indicating to the user, that the dose indicating mechanism and hence the drug delivery device is not in a standby mode but that a non-zero dose is actually set or is due to be dispensed.

The indicator may also comprise different indicating sections, each of which representing a different mode of the drug delivery device, its dose indicating mechanism or of its drive mechanism. Likewise to the dose indicating sleeve permanently coinciding or overlapping with the first window also the indicator may permanently overlap or coincide with the second window for each conceivable dose setting configuration. It is then of particular benefit, when the indicator comprises at least two different portions on its outer circumference to selectively show up in the second window for indicating a respective operational status of the dose indicating mechanism, of the drive mechanism or of the drug delivery device.

According to another embodiment the dose indicating sleeve is rotatable relative to the housing. The dose indicating sleeve may be axially fixed to the housing. It may only rotate relative to the housing while being substantially fixed to the housing in regard of its axial position. When axially fixed to the housing the dose indicating sleeve may comprise one or several dose indicating discs, each of which representing one or two digits of a two or three digit number. While one dose indicating disc may represent and comprise integer numbers ranging from (0, . . . , 9) another dose indicating disc may comprise consecutive numbers ranging from (1, . . . , 12). In this way, and by arranging such dose indicating discs axially adjacent with respect to each other all integer numbers between 0 and 120 can be displayed in the first window of the housing in general.

In effect, one of the dose indicating discs represents integer numbers from (0 . . . 9) whereas the other dose indicating disc represents numbers like (10, 20, 30, . . . , 120).

According to another embodiment the dose indicating sleeve is threadedly engaged with the housing. By way of a threaded engagement of dose indicating sleeve and housing the dose indicating sleeve may move relative and inside the housing according to a helical path. Said path is particularly governed by the mutually corresponding threads of dose indicating sleeve and housing. In order to show a large number of different dose sizes on its outer circumference, the dose indication provided on the outer circumference of the dose indicating sleeve may be arranged in a helical way, wherein the lead of said helical indication is identical or corresponds to the lead of the threaded engagement of dose indicating sleeve and housing.

Typically, the housing conceals the outer circumference of the dose indicating sleeve with the exception of that particular dose indication actually coinciding with the first window of the housing. The first window may comprise a protective screen or may simply feature a recess in the elongated housing of the dose indicating mechanism.

According to a further embodiment the dose indicating sleeve and the indicator are integrally formed. In this way, the indicator is simply a portion or a part of the dose indicating sleeve. However, the indicator operable to visually illustrate at least a standby mode of the drug delivery device is separated from the dose indication or dose indication scale of the dose indicating sleeve. By implementing the dose indicating sleeve and the indicator in a single component, no additional components have to be handled and assembled in the drug delivery device to provide the additional indicator functionality attained by the indicator and the second window.

In another embodiment the indicator is located at an axial end of the dose indicating sleeve. If the indicator is implemented as a zero dose configuration indicator, hence to visually indicate a standby mode of the drug delivery device, the indicator is typically located at that axial end of the dose indicating sleeve that faces away from the axial direction in which the dose indicating sleeve moves during a dose incrementing displacement. If for instance the dose indicating sleeve is subject to a distally directed displacement during dose incrementing the indicator is typically located at a proximal end of the dose indicating sleeve.

In addition to this also the second window is located proximal from the first window. As the dose indicating sleeve is subject to a helical and distally directed displacement during a dose incrementing dose setting operation the indicator is also subject to a distally directed displacement, thereby leaving the aperture of the second window.

In particular, when indicator and dose indicating sleeve are integrally formed, the indicator may also become subject to a helically-directed and hence tangential motion in correspondence with the threaded engagement of dose indicating sleeve and housing.

Moreover it is of particular benefit, that the axial size of the second window is substantially smaller than the axial distance between neighbouring threads of the threaded engagement of dose indicating sleeve and housing. In this way, it can be effectively prevented, that the indicator shows up repeatedly in the second window after e.g. the dose indicating sleeve has been rotated a complete revolution. The axial but also the tangential size of the second window and of the indicator is selected and designed such that the indicator unequivocally appears in the second window in one distinct position or configuration only. After a complete revolution of the dose indicating sleeve the indicator has travelled in axial direction to such an extent that exceeds at least the axial dimension of the second window and/or the axial dimension of the indicator itself.

Depending on the overall geometry and design of the dose indicating mechanism, of the drive mechanism and of the drug delivery device, it is likewise conceivable, that the indicator is for instance located at a proximal end of the dose indicating sleeve while the dose indicating sleeve is subject to a proximally directed displacement for dose incrementing and is further subject to an opposite, i.e. distally directed displacement during dose dispensing. In such a configuration it is intended, that the first window is located at a distally-directed offset from the second window. Hence, the second window then represents a distal window while the first window represents a proximal window of the dose indicating mechanism.

According to a further embodiment the indicator axially protrudes from the dose indicating sleeve. Hence, the indicator comprises or forms an appendix of the dose indicating sleeve to show up or to coincide with the second window of the elongated housing. Instead of an axial protrusion the indicator may also be formed by a visually discernible portion or section on the outer circumference of the dose indicating sleeve.

However, with an axially protruding indicator a displacement of the dose indicating sleeve and hence of the indicator may inherently reveal other components of the dose indicating mechanism or of the drive mechanism located underneath. By providing said other component with a colour, texture or some other visually discernible feature differing from the visual appearance of the indicator, said other component may equally indicate to the user or patient, that the dose indicating mechanism and hence the drug delivery device is actually in use and is hence not in a standby mode.

According to another embodiment the indicator also comprises at least one axially extending lateral edge. When designed as an axial protrusion or axial appendix, said lateral edge actually represents an outer or lateral margin of the indicator. In other embodiments, wherein the indicator is formed by a particular surface portion of the dose indicating sleeve, said lateral edge serves to visually separate and to visually distinguish adjacent portions of the dose indicating sleeve featuring different optical or visual appearances.

According to another embodiment the indicator also flushes with the outer circumference of the dose indicating sleeve. When formed as an axial protrusion or appendix of the dose indicating sleeve also the radially outwardly extending surface portion of the indicator may seamlessly complement the outer circumference and outer surface of the dose indicating sleeve.

In another embodiment the housing of the dose indicating mechanism and hence the housing of the drive mechanism or of the drug delivery device comprises a tubular-shaped body, typically serving as a main housing component and further comprises a closure member arranged at a proximal end of said body. In this way, a proximal housing component of the dose indicating mechanism may comprise at least two housing components, namely a body to be closed in proximal direction by means of a closure member.

Such a multi-component structure may be of particular benefit for the assembly of the device. Additionally, by means of different housing components, various configurations of the dose indicating mechanism, the drive mechanism or of the drug delivery device in its entirety can be provided, simply by replacing one of the housing components. The shape, geometry but also the colour of the housing component may represent a particular type of medicament, which may be arranged in the respective drug delivery device.

In a further embodiment, the first window is located in the body whereas the second window is located in at least one of the body and the closure member. In various embodiments the first window may be exclusively located in the body while the second window is located in the closure member. In this way and simply by interchanging a closure member by a differently-shaped closure member, the size of the second window may be modified to allow or to enable a different and varying functionality of the indicator for a respective different type of dose indicating mechanism or drug delivery device.

With the body and the closure member attached thereto it is also conceivable, that at least one of first and second windows is located in an interface section of body and closure member. Hence, for providing the second window it is conceivable, that e.g. a proximal end of the body comprises a recessed portion in a sidewall that corresponds with a correspondingly-shaped recessed portion of a sidewall of the closure member. By arranging the closure member and the body in such a way that respective recessed portions are adjacently located or substantially flush, a respective second window can be formed.

According to another aspect the invention also relates to a drive mechanism of a drug delivery device for dispensing of a dose of a medicament. The drive mechanism comprises a dose indicating mechanism as described above. Moreover, the drive mechanism comprises a piston rod to operably engage with a piston of a cartridge. Mutual engagement of the piston rod and the piston serves to displace the piston in a distal direction to expel a predefined amount of a medicament from the cartridge.

Typically, the piston seals the cartridge in axial proximal direction. The piston rod is however to be driven in axial distal direction by the drive mechanism. The piston rod is therefore operable to apply distally directed thrust or pressure to the piston of the cartridge for displacing the piston in distal direction relative to the cartridge for expelling and for dispensing of a predefined amount of the medicament.

The cartridge is typically located and fixed in the drug delivery device. When implemented as a reusable device, the cartridge is replaceable when empty. With a disposable drug delivery device the drive mechanism and the entire drug delivery device with the dose indicating mechanism is intended to be discarded after the medicament contained in the cartridge is used up.

The drive mechanism further comprises a drive sleeve which is switchable between a dose setting mode and a dose dispensing mode. Moreover, the drive sleeve is typically rotatably supported in the housing, for both setting of a dose as well as for dispensing of a dose. In the dose setting mode, the drive sleeve is operably disengaged from the piston rod. It is then rotatable relative to the housing in a dose incrementing direction.

Typically, dialing of the drive sleeve in dose incrementing direction may occur against the action of a spring element, such like a torsion spring or a helical spring. The mechanical energy transferred into the spring element via the drive sleeve may then be stored and saved by some kind of clutch mechanism. It is only upon switching of the drive sleeve and hence of the entire drive mechanism into the dose dispensing mode, that the drive sleeve operably engages with the piston rod for driving the piston rod in distal direction.

Hence, in the dose dispensing mode, the drive sleeve is operably engaged with the piston rod in order to transfer mechanical energy released from the spring element into a distally directed driving motion of the piston rod. When in dose dispensing mode the drive sleeve is rotatable relative to the housing in a dose decrementing direction, hence in a direction opposite to the dose incrementing direction, in which the drive sleeve can be rotated during dose setting. However, for correcting of a dose already set, the drive sleeve while being in dose setting mode may be also rotatable in dose decrementing direction.

For switching the drive mechanism between the dose setting and the dose dispensing mode the drive sleeve may be axially displaceable against the action of another spring element, thereby engaging and disengaging various clutch mechanisms or ratchet elements by way of which the drive sleeve may be released to rotate under the action of a relaxing spring element.

In general, the drive mechanism does not necessarily require a spring element to support distally directed displacement of the piston rod during dose dispensing. The dose indicating mechanism described herein can be applicable to a large variety of purely mechanically implemented or semi-automated drive mechanisms of drug delivery device, in particular of pen-type injectors. It may also be applicable to drive mechanisms, wherein the drive sleeve and/or the dose indicating sleeve is at least partially extendable from a proximal end of the housing and wherein a user has to apply a distally directed force or thrust to an actuation member for axially reinserting the dose indicating sleeve into the housing.

According to another embodiment, the dose indicating sleeve at least encloses an axial section of the drive sleeve. Moreover, the dose indicating sleeve is rotatably engaged with the drive sleeve by means of at least one radially extending protrusion engaged with a correspondingly shaped radial recess. Here, it is conceivable, that the dose indicating sleeve comprises at least one axially extending radial groove at an inside facing sidewall portion whereas the drive sleeve comprises at least one correspondingly shaped, radially outwardly extending protrusion or rib. Said protrusion or rib may even extend in axial direction along the complete extension of the drive sleeve. In this way, any rotational displacement or movement of the drive sleeve can be unalterably transferred to the dose indicating sleeve in both directions of rotation.

Hence, the dose indicating sleeve may rotate in unison with the drive sleeve in both, hence in the dose incrementing direction as well as in the dose decrementing direction. Consequently, the dose size indicating numbers presented in the first window will increase as the drive sleeve and/or the dose indicating sleeve rotate in dose incrementing direction during setting of a dose. During dose dispensing however, the drive sleeve and/or the dose indicating sleeve are subject to a rotation in dose decrementing direction. The number illustrated in the first window will then count down until a zero-dose configuration is reached at the end of the respective dispensing procedure.

In order to provide a rather smooth and homogeneous transfer of rotational motions or torque between the drive sleeve and the dose indicating sleeve it may be of particular benefit, when drive sleeve and dose indicating sleeve comprise at least two or even more correspondingly-shaped protrusions and recesses, e.g. equidistantly distributed along the outer and inner circumference of drive sleeve and dose indicating sleeve, respectively.

It is also conceivable, that it is the dose indicating sleeve comprising at least one radially inwardly extending protrusion or axially extending rib at an inward facing sidewall portion whereas the correspondingly-shaped radial recess, e.g. in form of an axial groove is provided at the outer circumference of the drive sleeve extending through the dose indicating sleeve.

Even though an immediate mechanical interaction between drive sleeve and dose indicating sleeve is described here, it is also conceivable, that transfer of a rotational motion between drive sleeve and dose indicating sleeve is realized via at least one additional element, e.g. by means of an intermediate sleeve or some other kind of torque transmitting means radially disposed between drive sleeve and dose indicating sleeve.

In another embodiment the indicator is displaceable outside the second window or beyond the second window to reveal the drive sleeve located underneath. In this embodiment the indicator and the drive sleeve typically comprise different visual appearances. Hence, the drive sleeve and the indicator may comprise different colours. Even though the drive sleeve may be axially displaceable between a dose setting position and a dose dispensing position it may always coincide with the second window. In effect, the appearance of the drive sleeve in the second window may be only and exclusively prevented by the indicator to selectively conceal the drive sleeve in the second window, in particular when the drive mechanism reaches a standby configuration.

Certain aspects of the present invention relate to a drug delivery device for dispensing a medicament. The drug delivery device comprises a drive mechanism as described above and further has a cartridge holder to accommodate a cartridge filled with the medicament to be dispensed by the drug delivery device. The cartridge holder may be fixed to the drive mechanism, hence to the housing thereof either releasably or non-releasably. When designed as a disposable drug delivery device, the cartridge holder is non-releasably attached and fixed to the housing. With reusable drug delivery devices, the cartridge holder is typically releasably attached to the housing in order to replace the cartridge when empty.

In a further embodiment of the drug delivery device the device is further equipped with a cartridge filled with the medicament. Hence, the cartridge is arranged in the housing of the drug delivery device, typically in the cartridge holder thereof.

In the present context, the distal direction points in the direction of the dispensing end of the device, where, preferably a needle assembly is provided having a double-tipped injection needle that is to be inserted into biological tissue, typically into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which.

DETAILED DESCRIPTION

Figure 6:
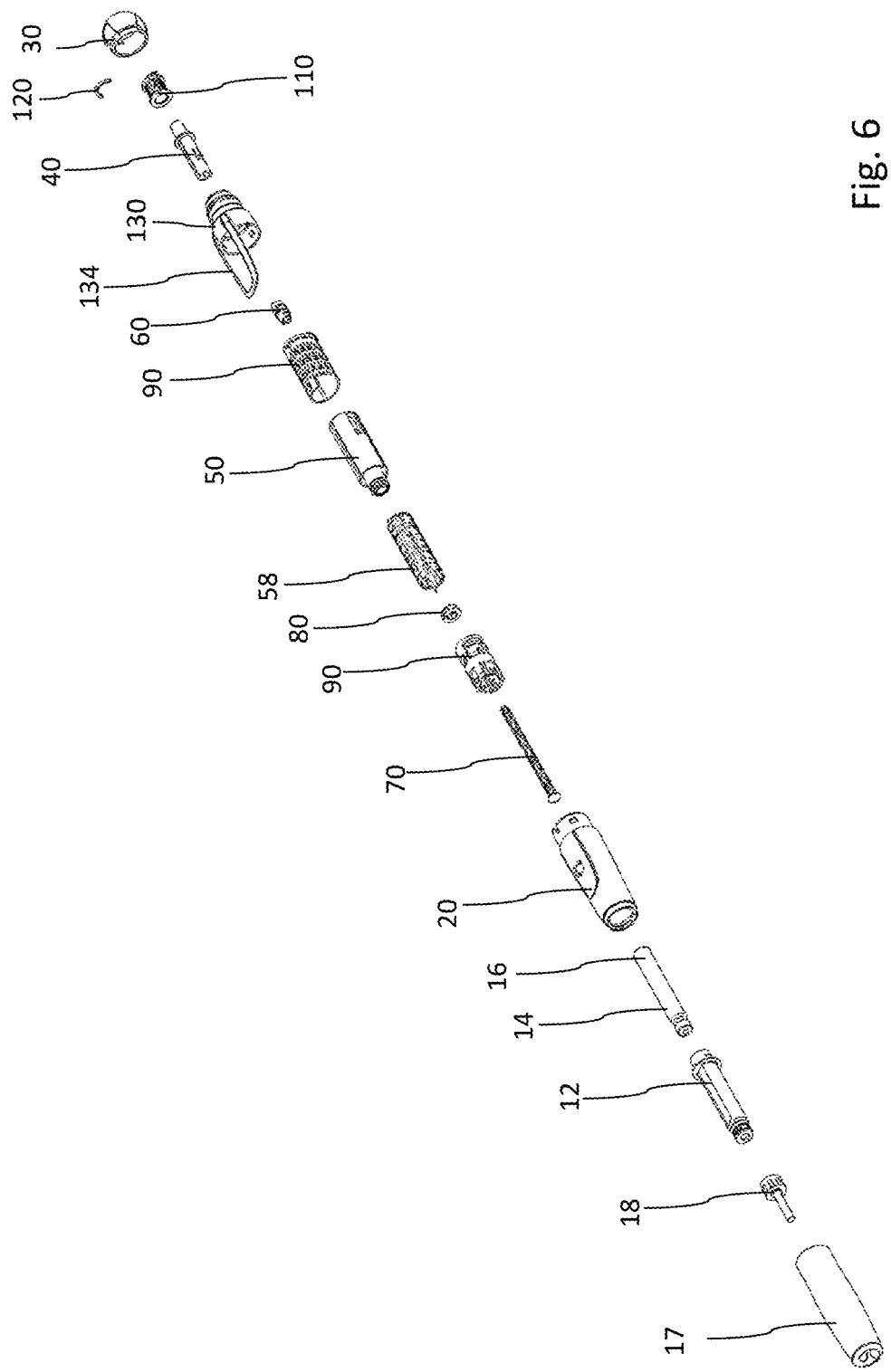
FIG. 6 is illustrative of an exploded view of the various components of the drug delivery device.

In FIG. 6, a drug delivery device 10 is illustrated in an exploded view. The drug delivery device 10 of pen-injector type and comprises a substantially cylindrical and axially elongated shape. Throughout the Figures, the axial distal direction is denoted with reference number 1 and the opposite proximal direction is denoted with reference number 2. The drug delivery device 10 which is also shown in an assembled configuration in FIG. 1 in longitudinal cross section comprises a drive mechanism 3 arranged in a proximal body 20 generally providing a housing of the drive mechanism 3. In distal direction 1, the body 20 is connected with a cartridge holder 12 which is adapted to accommodate and to receive a cartridge 14 containing the medicament to be dispensed by the drug delivery device 10. The cartridge 14 typically comprises a vitreous barrel of cylindrical shape which is sealed in distal direction by a pierceable sealing member, such like a septum.

In proximal direction 2, the cartridge 14 is sealed by a piston 16 slideably arranged in the vitreous barrel of the cartridge 14. Displacement of the piston 16 in distal direction 1 leads to a respective built-up of a fluid pressure inside the cartridge 14. When the distal outlet of a cartridge 14 is connected with e.g. a needle assembly 18, as for instance indicated in FIG. 1, a predefined amount of the liquid medicament contained in the cartridge 14 can be expelled and dispensed via an injection needle of the needle assembly 18, which is not particularly illustrated here.

Figure 1:
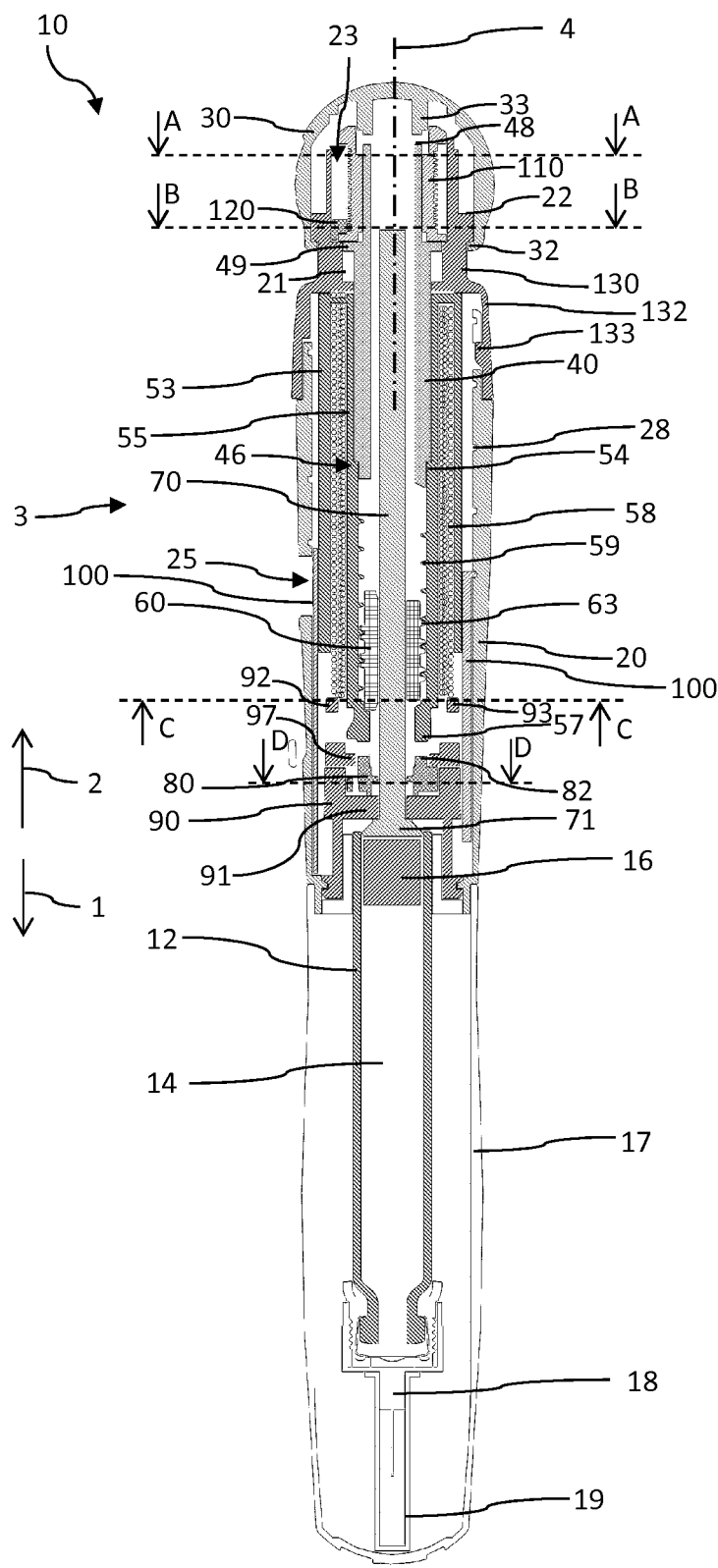
FIG. 1 schematically illustrates a pen-type injection device in a longitudinal cross section, FIG. 2 schematically shows a cross-section through the device according to FIG. 1 along A-A.

In FIG. 1, an inner needle cap 19 to protect the double-tipped injection needle is schematically indicated. The needle assembly 18 is typically arranged on a distal end portion of the cartridge holder 12. Typically, a distally located socket of the cartridge holder 12 and the needle assembly 18 comprise mutually corresponding threads to screw the needle assembly 18 onto the cartridge holder 12 in a releasable and removable way.

The cartridge holder 12 is to be protected and covered by a protective cap 17. Prior to setting and/or dispensing of a dose, the protective cap 17 as well as the inner needle cap 19 are to be removed. After dispensing or injecting of the medicament into biological tissue, the needle assembly 18 is typically to be discarded and the distal end of the drug delivery is to be covered by the protective cap 17.

The drive mechanism 3 as illustrated in an exploded view in FIG. 6 and as shown in cross section in FIG. 1 in its fully assembled configuration comprises numerous functional components by way of which a dose of variable size can be set and subsequently dispensed.

The dose dispensing procedure comes along with a distally directed advancing displacement of the piston rod 70 relative to the body 20. The drive mechanism 3 therefore comprises at least a body 20, a piston rod 70 and a drive sleeve 50 which can be released and operably engaged with the piston rod 70 for selectively setting and dispensing of a dose. Moreover, the drive mechanism 3 comprises a dose limiting member 60 which is engaged with the drive sleeve 50 as well as with the piston rod 70. Mutual engagement of the dose limiting member 60 with both, the drive sleeve 50 and with the piston rod 70 is such, that the dose limiting member is displaced in axial direction, hence in distal and/or proximal direction 1, 2 relative to the drive sleeve 50 when the drive sleeve 50 rotates relative to the piston rod 70 during a dose setting procedure.

Apart from the drive sleeve 50, the dose limiting member 60 and the piston rod 70, the drive mechanism 3 comprises a number of further components as illustrated in FIG. 1. These components together with the actuation member 30 as shown in inter alia serve to visually indicate the size of set dose to a user and further serve to transfer a rotational and/or axial displacement of the user-operated actuation member 30 into respective rotational and/or axial displacement of the drive sleeve 50 for dose setting and/or dose dispensing purpose.

It is to be noted here, that the embodiment as illustrated in FIGS. 1 to 10 is only exemplary for one of a plurality of conceivable drive mechanisms that may be equipped with the dose indicating mechanism 214 as shown in FIGS. 11 to 17.

In the following, setting of a dose is described.

Figure 7:
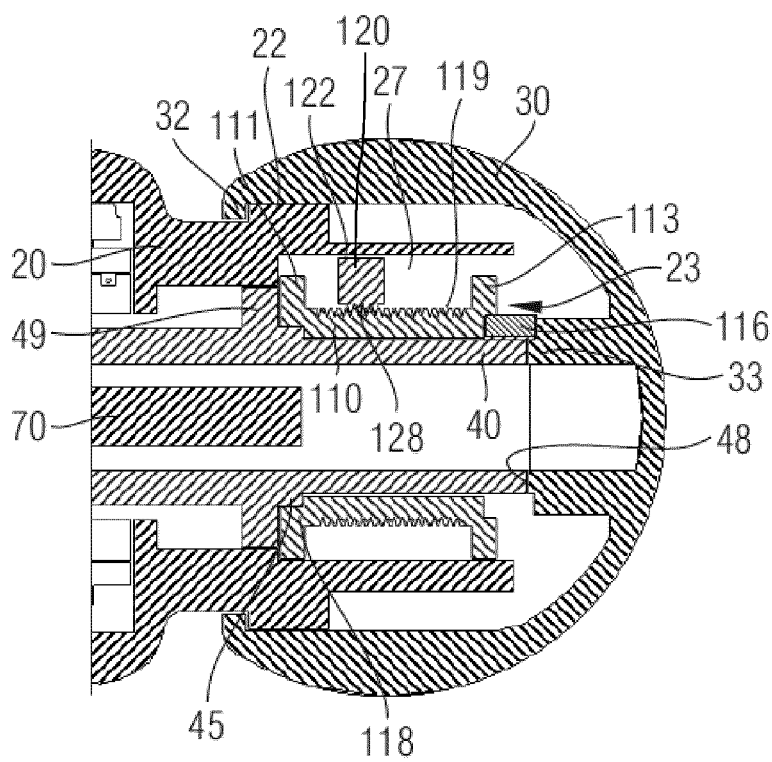
FIG. 7 shows a longitudinal cross-section through the proximal end of the device according to FIG. 1.
Figure 8:
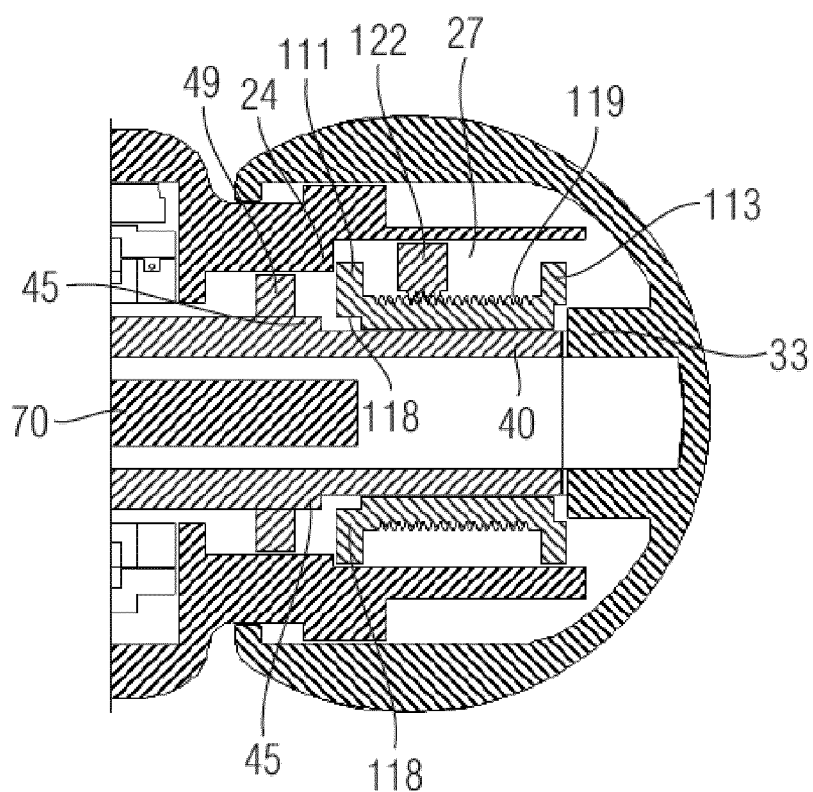
FIG. 8 shows the proximal end according to FIG. 7 with the actuation member depressed in distal direction.

For setting of a dose, the user grips the actuation member 30 located at the proximal end of the body 20. The actuation member 30 comprises a radially inwardly extending flange portion 32 at its distal end as indicated in FIGS. 7 to 9, which in a proximally located configuration according to FIG. 7 axially abuts with a radially outwardly extending rim 22 of the body 20.

The body 20 further comprises a proximal and tubular shaped receptacle 23 to receive a substantially tubular shaped last dose sleeve 110. The last dose sleeve 110 comprises a radially outwardly extending distal flange 111 extending on a distal end thereof. With this distal flange 111 the last dose sleeve 110 abuts in distal direction with a radially inwardly extending socket 24 of the body 20. Moreover, by means of the distal flange 111 the last dose sleeve 110 is also radially guided and confined in the proximal receptacle 23 of the body 20.

Furthermore, by means of its flange portion 32 the actuation member 30 may be snapped on the proximal end of the body 20 and may therefore positively engage with the body 20 at least in proximal direction 2. In particular, the actuation member 30 is cup-shaped and surrounds and closes the receptacle 23 of the body 20 in proximal direction when assembled thereon.

Figure 9:
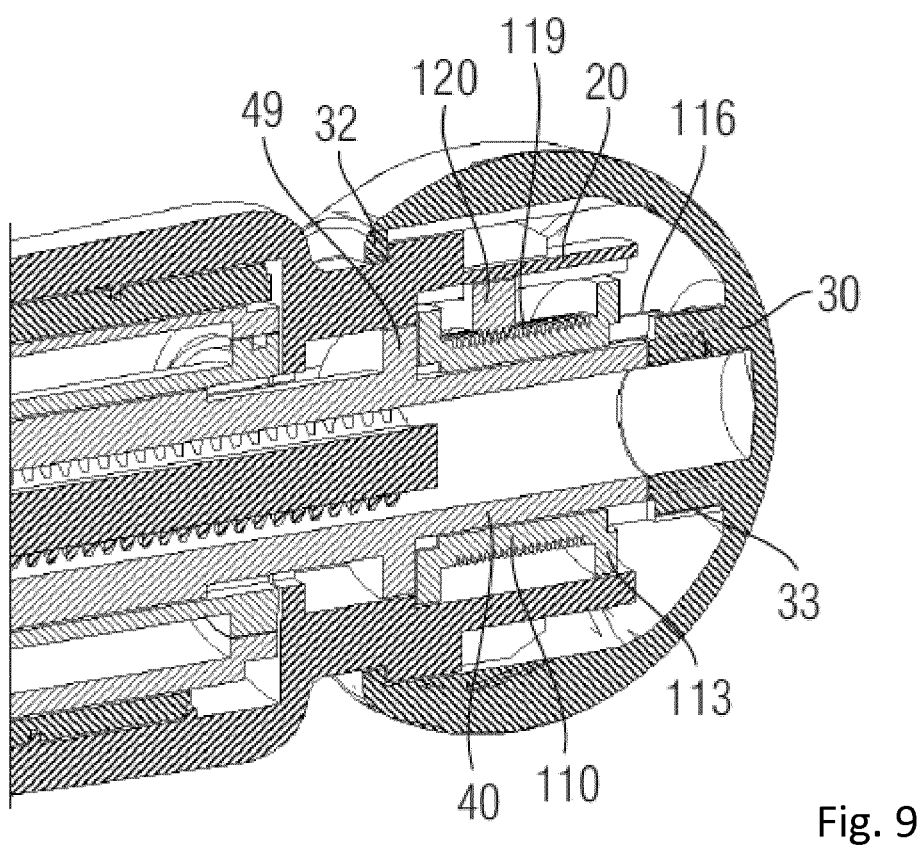
FIG. 9 shows a partially cut and perspective illustration of the proximal end of the drug delivery device and FIG. 10 shows a side view of the outer housing of the drug delivery device according to FIG. 1.

From a proximal portion of the last dose sleeve 110, there extend two helically shaped resilient spring elements 116 integrally formed with the last dose sleeve 110 as indicated in FIG. 9. These spring elements 116 abut with a proximal and inward facing portion of the hollow actuation member 30 and therefore keep the actuation member 30 in its initial, hence proximally located configuration as illustrated for instance in FIG. 7.

Figure 2:
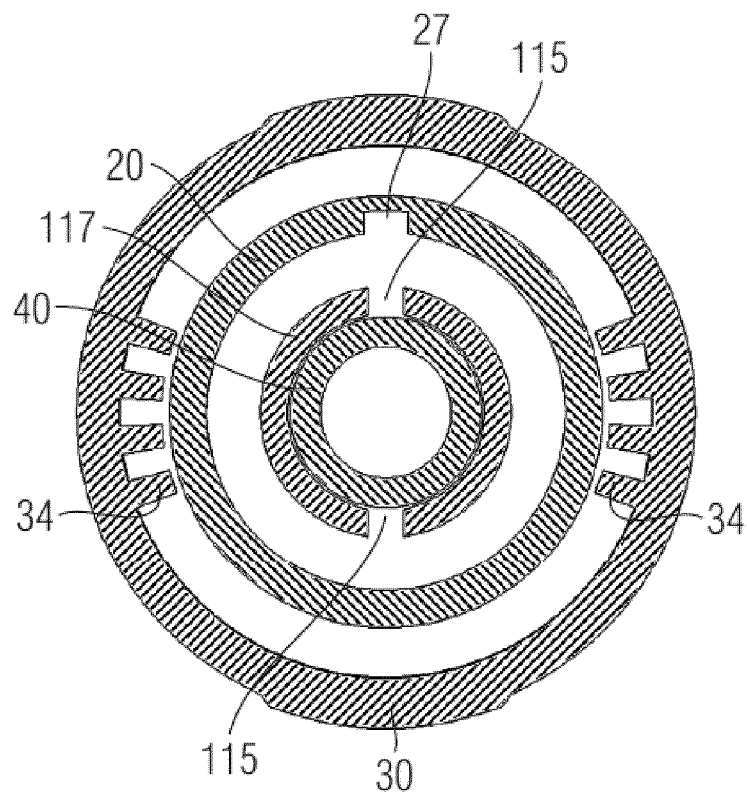

In this initial configuration which coincides with and specifies a dose setting mode of the drive mechanism 3, axially inwardly extending journals 33 of the actuation member 30 extend into two respective diametrically oppositely located recesses 115 of a proximal rim 117 of the last dose sleeve 110 as indicated in FIG. 2. In this way, the last dose sleeve 110 and the actuation member 30 are rotatably coupled in the initial configuration of the actuation member 30.

In this configuration, rotation of the actuation member 30 leads to a corresponding rotation of the last dose sleeve 110. In the dose setting mode, the last dose sleeve 110 is further rotatably engaged and rotatably coupled with a clutch 40 as becomes apparent from a combination of FIGS. 3 and 7. As in particular illustrated in the cross section B-B in FIG. 3, the inside facing portion of the distal end of the last dose sleeve 110 comprises a toothed surface 118 that meshes with radially outwardly extending teeth 45 of the clutch 40.

This way, the last dose sleeve 110 and the clutch 40 extending there through and hence providing an axis of rotation for the last dose sleeve 110, are rotatably fixed and are therefore rotatably engaged. Consequently, a rotation of the actuation member 30 leads to an equal rotation of the clutch 40 during a dose setting procedure. The clutch 40 is further connected with the drive sleeve 50. Hence, a distal portion of the clutch 40 is located inside the tubular shaped and hollow drive sleeve 50.

Here, and independent of the mode of operation of the drive mechanism 3, the clutch 40 and the drive sleeve 50 are axially fixed as well as rotatably fixed with respect to each other. Hence, a rotation of the clutch 40 is unalteredly transferred to the drive sleeve 50. Accordingly, also an axial displacement of the clutch 40 is unalteredly transferred to a respective axial displacement of the drive sleeve 50. The drive sleeve may for instance comprises two diametrically opposite longitudinal grooves in its inside facing sidewall, that are adapted to mate and to receive correspondingly shaped and radially outwardly extending ribs of the clutch 40.

Moreover, the clutch 40 comprises at least one or at least two oppositely located radially outwardly extending and resiliently deformable snap portions 46 adapted to engage with a correspondingly shaped recess 54 of the drive sleeve 50 as schematically illustrated in FIG. 1. By means of the mutually corresponding ribs 44 and grooves 52 as well as due to the snap portions 46 engaged with the recess 54, a rotational and longitudinal engagement of clutch 40 and drive sleeve 50 can be provided.

The drive sleeve 50 can be rotated inside and relative to the body 20 in a dose incrementing direction 5 against the action of a helically shaped torsion spring element 58. One end, e.g. the proximal end of the helical spring 58 is attached and coupled to the proximal end of the drive sleeve 50 while an opposite, e.g. distal end of the helical spring 58 is fastened to the body 20. A dose incrementing rotation of the actuation member 30 therefore leads to a corresponding rotation of the drive sleeve 50 against the restoring force of the helical spring 58 almost completely surrounding the drive sleeve 50.

Figure 4:
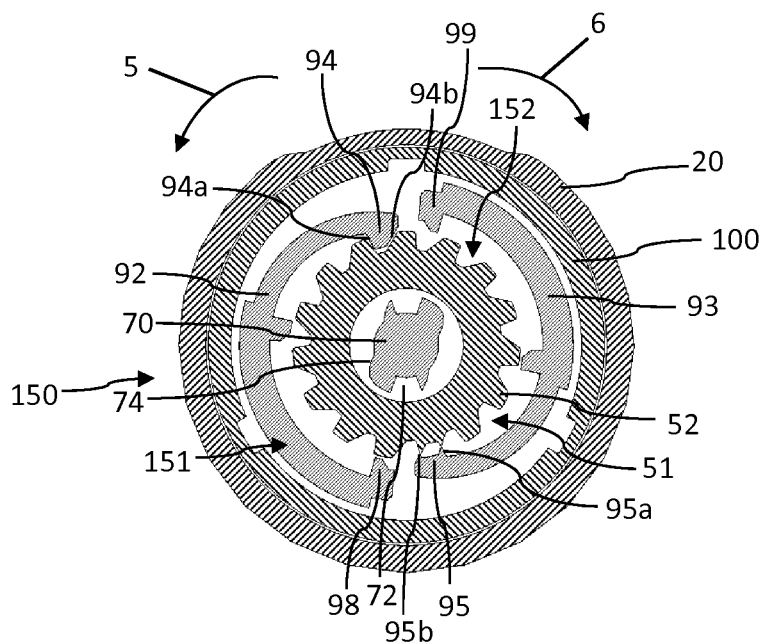
FIG. 4 is illustrative of a cross-section through the device according to FIG. 1 along C-C.

As shown in the cross-section of FIG. 4 the drive mechanism 3 is equipped with a particular ratchet mechanism 150 that may be generally implemented with a variety of different drive mechanism featuring a rotatable drive sleeve. As shown in FIG. 4, the drive sleeve 50 comprises a radially outwardly extending toothed profile 51 near a distal end section. The toothed profile 51 engages with mutually corresponding and radially inwardly extending first and second ratchet elements 94, 95 of first and second ratchet members 92, 93 of a first ratchet body 151, respectively. The first ratchet body 151 is fixed to the body 20 and is integrally formed with a base member 90 that is fixedly attached to a distal end of the body 20. The base member 90 further comprises radially inwardly extending protrusions 91 forming a through opening therebetween that coincides with the longitudinal axis 4 of the device 10 and which serves to axially guide the piston rod 70 relative to the base member 90 and hence relative to the body 20.

Figure 4A:
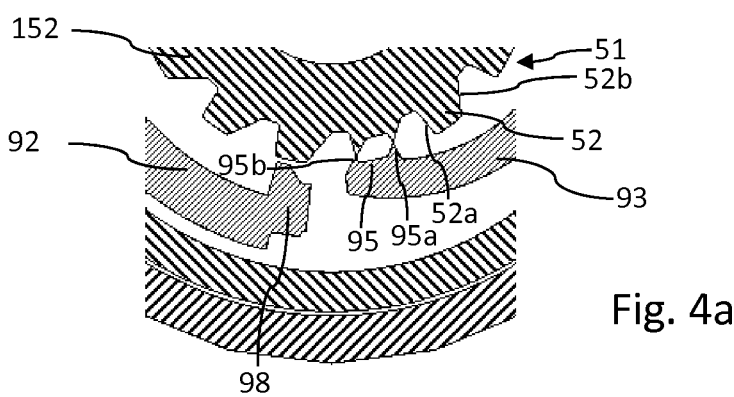
FIG. 4a shows an enlarged section of FIG. 4.
Figure 5:
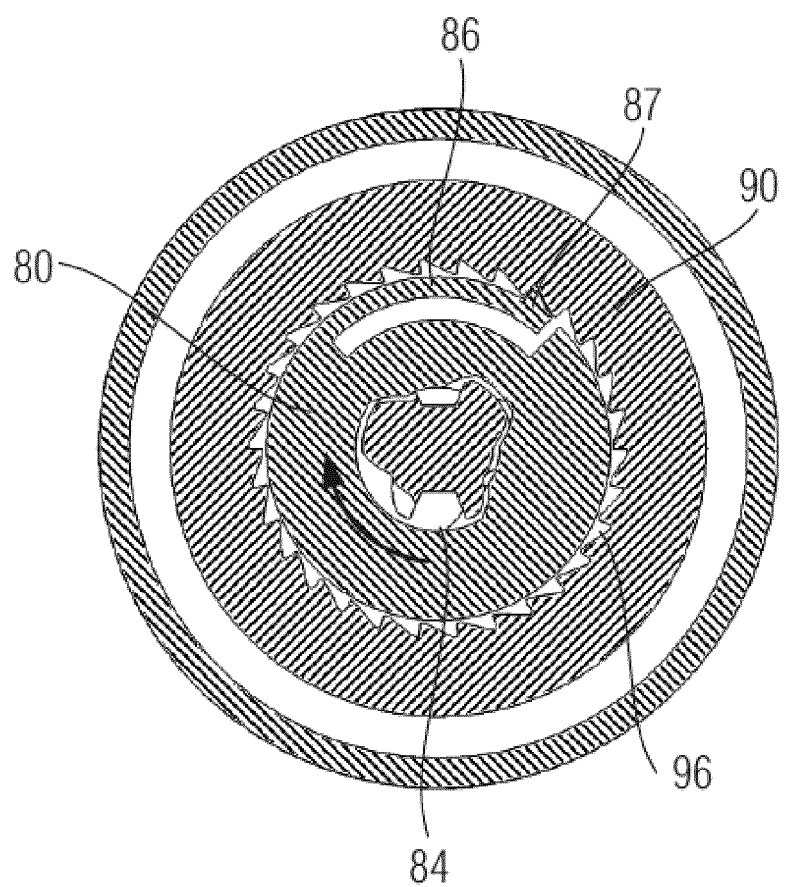
FIG. 5 shows a cross-section along D-D of the device according to FIG. 1.

The distal end of the drive sleeve 50 represents or comprises a second ratchet body 152 featuring a toothed profile 51. As indicated in FIG. 4, first and second ratchet elements 94, 95 of the first ratchet body 151 alternately engage with the toothed profile 51 of the drive sleeve 50 as the drive sleeve 50 is either rotated in dose incrementing direction 5 or in dose decrementing direction 6. As further indicated in the enlarged view of FIG. 4a, the first ratchet element 94 is somewhat triangular shaped and comprises a rather steep stop portion 94a facing in dose incrementing direction and being adapted to abut and to engage with a correspondingly shaped and rather steep edge 52a of the toothed profile 51.

When the drive sleeve 50 is rotated in dose incrementing direction 5 against the action of the spring element 58 the first ratchet element 94 regularly engages and meshes with consecutive teeth 52 of the drive sleeve 50. Since the stop portion 94a and the steep edge 52a of the first ratchet element 94 and the toothed profile 51 almost extend radially outwardly at a fairly steep angle a kind of a rotational interlock can be provided as the radially inwardly extending first ratchet element 94 with its stop portion 94a engages with a correspondingly shaped steep edge 52a of the toothed profile 51.

In a similar way also the second ratchet element 95 consecutively meshes or consecutively engages with the toothed profile 51 of the drive sleeve 50. Like the first ratchet element 94 also the second ratchet element 95 comprises a radially extending and hence a rather steep stop portion 95a facing in dose incrementing direction 5 to abut against the steep edge 52a of the toothed profile 51.

Adjacent to the stop portion 95a, the second ratchet element 95 comprises a radially inwardly extending tilted ramp portion 95b facing in dose decrementing direction 6 that engages with the ramp portion 52b of the toothed profile 51 facing in dose incrementing direction 5 when the drive sleeve 50 is rotated in dose incrementing direction 5.

The tipped and radially inwardly facing end of the ramp portion 95b may further mesh with the ramp portion 52b as the second ratchet body 152 is rotated in dose incrementing direction 5 relative to the first ratchet body 151. Here, the second ratchet element 95 provides a braking or retarding effect.

Likewise, also the first ratchet element 94 comprises a ramp portion 94b facing in dose decrementing direction 6 to engage and to mesh with the ramp portion 52b of the second ratchet body's 152 toothed profile 51.

The slope of the ramp portions 52b, 95b and 94b is adjusted and designed in accordance with the resilient properties of the arc-shaped and radially deformable ratchet members 92, 93. In this way, a well-defined mechanical interlocking of first and second ratchet elements 94, 95 with the toothed profile 51 can be obtained. By the geometric shape of ramp portions 52b, 94b and 95b mechanical resistance for dose incrementing or dose decrementing dialing of the drive sleeve 50 relative to the body 20 can be adjusted whereas the geometric shape and position of the toothed profile's 51 steep edges 52a engaging with correspondingly shaped stop portions 94a, 95a of first and second ratchet elements 94, 95 may provide an adjustment of maximum holding and retention forces of respective torques between drive sleeve 50 and body 20 that are required to overrule the ratchet mechanism 150 for dose correcting purpose.

As further illustrated in FIG. 4, first and second ratchet members 92, 93 each comprise a radially inwardly extending protrusion 98, 99 at an end portion opposite to the first and second ratchet elements 94, 95. These protrusions 98, 99 serve to radially guide and to radially fix the drive sleeve 50 inside the first ratchet body 150.

By rotating the drive sleeve 50 in a dose incrementing direction 5 the first ratchet element 94 of the first ratchet member 92 and the second ratchet element 95 of the second ratchet member 93 alternately engage and mesh with consecutive teeth 52 of the drive sleeve's 50 toothed profile 51. As illustrated in FIG. 4, the first and second ratchet elements 94, 95 of first and second ratchet members 92, 93 are circumferentially offset by e.g. half of a period of consecutively arranged teeth 52. In this way, the size of discrete steps for setting of a dose can be effectively reduced without the necessity to make use of respective small sized teeth 52 and ratchet elements 94, 95.

Additionally, the first and second ratchet elements 94, 95 also provide a retarding force acting on the rotating drive sleeve 50. In this way, a predefined braking or friction force can be applied to the drive sleeve 50 in order to at least partially compensate an impact of the spring element 58 on the rotational behaviour of the drive sleeve 50. Since the stop portions 94a, 95a differ in shape from the ramp portions 94b, 95b and since the steep edges 52a of the toothed profile differ in shape from ramp portions 52b retarding and holding forces of different magnitude can be provided when the drive sleeve is rotated in dose incrementing direction 5 and in dose decrementing direction 6. In this way a supporting effect of the helically shaped torsion spring element 58 on a dose decrementing rotation of the drive sleeve 50 can be counteracted or can be at least reduced.

A dose incrementing action governed by a rotation of the actuation member 30 and a corresponding rotation of the drive sleeve 50 also leads to a corresponding rotation of a dose indicating sleeve 100. The dose indicating sleeve 100 is threadedly engaged with the body 20 and comprises numerous dose indications 104, typically in form of dose indicating numbers at its outer circumference, as for instance indicated in FIG. 10. The numbers are arranged in a helical way on the outer circumference of the dose indicating sleeve 100. Moreover, the dose indicating sleeve 100 comprises an outer thread engaged with the inside facing sidewall portion of the body 20, in particular with the inner thread 28 of the body 20 as indicated in FIG. 1.

A rotation of the drive sleeve 50 unalteredly transfers to a respective rotation of the dose indicating sleeve 100 by way of a keyed or splined engagement adapted to directly transfer a rotation the drive sleeve 50 to the dose indicating sleeve 100 and vice versa and supporting an axial displacement of the drive sleeve 50 relative to the dose indicating sleeve 100.

The drive sleeve 50 as indicated in FIG. 1 comprises an inner sleeve portion 55 with an inner or internal thread 59 to engage with the external thread 63 of the dose limiting member 60. Moreover, the drive sleeve 50 also comprises an outer sleeve portion 53 extending coaxially with the inner sleeve portion 55 and forming an annular and axially extending recess therebetween. Said recess is particularly adapted to receive the helical spring element 58. It is in particular the distal portion of the outer sleeve portion 53 which is keyed or splined engaged with the dose indicating sleeve 100. The outer sleeve portion 53 may comprise one or several radially outwardly extending ribs or protrusions to engage with correspondingly shaped and axially extending grooves 102 at an inside facing sidewall portion of the dose indicating sleeve 100 as shown for instance in FIG. 4. In this way the drive sleeve 50 and the dose indicating sleeve 100 are rotatably coupled but remain axially displaceable relative to each other.

When during a dose setting procedure the actuation member 30 is rotated relative to the body 20 the drive sleeve 50 is rotated in the same way and due to the splined engagement of drive sleeve 50 and dose indicating sleeve 100 also the dose indicating sleeve 100 will always instantly show a corresponding dose size indicating number 104, e.g. representing an amount of international units IU in a dose displaying or dose indicating window 25 of the body 20. As indicated for instance in FIG. 10, the dose indicating window 25 may comprise a recess or a through opening in the sidewall of the body 20.

Decrementing of the dose, hence dialing the actuation member 30 in an opposite sense of rotation, leads to a respective counter-rotation of the drive sleeve 50. Consequently, also the dose indicating sleeve 100 rotates in the opposite sense, hence in a dose decrementing direction 6 and a correspondingly decreasing dose indicating number 104 will show up in the window 25.

In the following dispensing of a dose is described.

Once a dose has been set, the drive mechanism 3 may be switched into a dispensing mode by depressing the actuation member 30 in distal direction 1 as for instance indicated in FIG. 8. Here, the actuation member 30 actually fulfils a double or even a triple function. First of all, the actuation member 30 serves to transfer an angular momentum to the last dose sleeve 110 and/or to further functional components of the drive mechanism 3 operably engaged therewith. Second, the actuation member 30 controls and triggers a dose dispensing procedure. Third, the actuation member 30 actually seals and closes a proximal end of the body 20 of the drive mechanism 3 and/or of the drug delivery device 10.

Moreover, the present arrangement of the actuation member 30 also allows for a priming of the drive mechanism 3 during manufacturing of the drug delivery device 10, when a cartridge 14 is to be readily arranged therein. In the process of assembly of the device 10, the piston rod 70 can be advanced in distal direction 1 to directly abut with the piston 16 of the cartridge 14. Here, a proximal end of the piston rod 70 is accessible, e.g. by means of a separate push rod, which is actually not illustrated here. It is then after bringing the piston rod 70 in operative engagement with the piston 16 of the cartridge 14 that the actuation member 30 is finally assembled to the body 20 thereby closing the proximal receptacle 23 thereof.

By displacing the actuation member 30 in distal direction 1, the resilient spring elements 116 of the last dose sleeve 110 will be compressed. At the same time, the axially inwardly protruding journals 33 of the actuation member 30 will further extend through the longitudinal recesses 115 of the last dose sleeve 110 and will push a proximal rim 48 of the clutch 40 in distal direction 1 as becomes apparent from a comparison of FIGS. 7 and 8.

Figure 3:
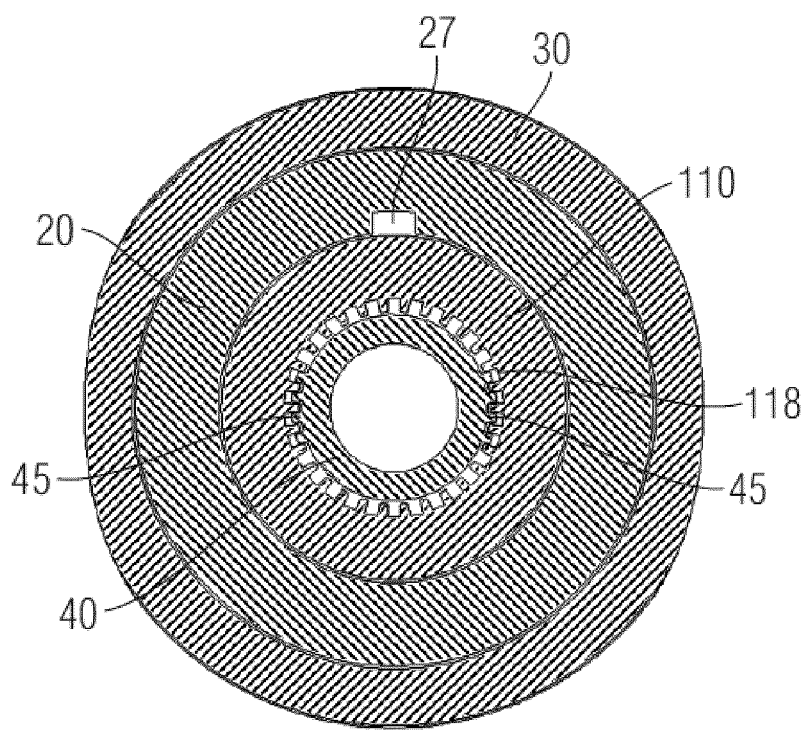
FIG. 3 shows a cross-section along B-B.

Due to this distally directed displacement of the clutch 40, radially outwardly extending teeth 45 of the clutch 40, as shown in FIG. 3, do no longer engage with the inner toothed surface 118 of the last dose sleeve 110. As a consequence, the clutch 40 is rotatably disengaged from the last dose sleeve 110 and is free to rotate.

At the same time radially inwardly extending teeth 34 provided at the inside facing sidewall portion of the actuation member 30 engage with a toothed ring 26 provided on the outer circumference of the proximal portion of the body 20. Since the teeth 34 get in engagement with the toothed ring 26 by the axially and distally directed displacement of the actuation member 30 relative to body 20, the actuation member 30 is rotatably locked to the body 20 during a dose dispensing action. Consequently, the last dose sleeve 110, which is still rotatably engaged with the actuation member 30, cannot rotate during the dose dispensing procedure.

Since the clutch 40 is not only rotatably but also axially coupled and connected with the drive sleeve 50, the distally directed displacement of the clutch 40 is unalteredly transferred to a respective distally directed displacement of the drive sleeve 50.

As further indicated in FIG. 1, the clutch 40 is biased in proximal direction 2 by means of at least one spring element 21, which may be integrally formed with the body 20. The spring element 21 can be resiliently deformed and biased in axial, hence distal direction 1 by the radially extending flange 49 of the clutch 40. Since the clutch 40 is to be displaced in distal direction 1 against the action of the spring element 21, a coupling of the drive sleeve 50 with a drive member 80 is only active as long as a respective distally directed force is applied to the actuation member 30, e.g. during a dose dispensing procedure. In particular, the member may comprise a drive nut.

The distally directed displacement of the drive sleeve 50 is limited by the drive member 80 as indicated in FIG. 1. When in mutual axial abutment, the drive sleeve 50 and the drive member 80 are rotatably engaged while the drive sleeve 50 with its toothed profile 51 is disengaged from the ratchet members 92, 93 of the base member 90. Mutual rotatable engagement of drive sleeve 50 and drive member 80 is achieved by mutually corresponding teeth or comparative interlocking members provided on a distal crown wheel 57 of the drive sleeve 50 and on a proximal crown wheel 82 of the drive member 80, respectively. Hence, the proximal face of the drive member 80 comprises a crown wheel 82 operable to engage with a correspondingly shaped crown wheel 57 provided on the distal face of the drive sleeve 50.

Typically, the axial extension of mutually corresponding crown wheels 82, 57 is such, that a rotational engagement of drive sleeve 50 and drive member 80 is achieved before the ratchet mechanism 151 between base member 90 and drive sleeve 50 is released due to a distally directed displacement of the drive sleeve 50 relative to the base member 90 and hence relative to the body 20. In this way, a substantially slipless coupling of drive sleeve 50 and drive member 80 can be achieved.

An early or premature release of the actuation member 30 prior to a termination of the dose dispensing procedure will lead to an immediate proximally directed displacement of the clutch 40 relative to the body 20 under the effect of the biased spring element 21. Consequently, the ratchet mechanism 151 will reengage thereby rotatable locking the drive sleeve 50 relative to the body 20 and keeping the energy stored in the biased helical spring 58.

The drive member 80 is typically axially fixed in the base member 90 by means of a radially inwardly extending flange portion 97 as shown for instance in FIG. 1.

The base member 90 comprises two diametrically oppositely arranged and radially inwardly extending protrusions 91 that engage with correspondingly shaped grooves 72 of the piston rod 70. The piston rod 70 extends through the base member 90 in axial direction and comprises a pressure foot 71 at its distal end to directly engage with the piston 16 of the cartridge 14. The radially inwardly extending protrusions 91 of the base member 90 may further be part of a web or flange portion featuring a through opening, through which the piston rod 70 extends axially. The pressure foot 71 may be rotatable with respect to the piston rod 70. But when the piston rod 70 is non-rotatably engaged with the body 20, a rotatably supported pressure foot 71 is not required in general.

The piston rod 70 comprises an outer thread 74 which is only threadedly engaged with an inner thread 84 of the drive member 80.

When rotatably coupled, the drive sleeve 50 under the action of the biased helical spring 58 transfers an angular momentum to the drive member 80, which in turn rotates around the axially fixed piston rod 70. The rotation of the drive member 80 then serves to advance the piston rod 70 in distal direction 1 for expelling of a dose of the medicament.

The drive member 80 also comprises a ratchet member 86 having a circumferentially extending arm resiliently deformable in radial direction. At the free end of the ratchet member 86 a radially outwardly extending tooth 87 is located which is adapted to mesh with a correspondingly shaped toothed surface or toothed profile 96 provided at the inside facing wall of the base member 90. As indicated in cross section in FIG. 5 the ratchet member 86 and the toothed structure 96 are configured such, that only a dose decrementing rotation 6 of the drive member 80 is allowed while a counter-directed rotation of the drive member 80 is effectively inhibited. This way, the piston rod 70 is only displaceable in distal direction 1 but not in proximal direction with respect to the body 20.

The ratchet member 86 of the drive member 80 and the toothed structure 96 of the base member 90 provide an effective anti-backup feature.

Moreover, when rotating in a dose decrementing direction during a dose dispensing procedure, the ratchet member 86, and in particular its radially outwardly extending free end consecutively meshes with the geared or toothed profile of the base member 90 or with a correspondingly shaped inner surface portion of the body 20. The mutual engagement of the ratchet member 86 sliding along the toothed structure 96 also generates an audible click sound inherently indicating to the user, that the dispensing procedure is actually in progress.

For limiting a dose setting as well as a dose dispensing procedure the drive mechanism 3 further comprises a dose limiting member 60 slideably arranged on the piston rod 70 in axial direction and threadedly engaged with the drive sleeve 50. The dose limiting member 60 comprises the shape of a half-shell and therefore only partially surrounds the piston rod 70 in circumferential or tangential direction. The dose limiting member 60 comprises a radially inwardly extending gliding portion by way of which the dose limiting member 60 may slide or glide along the groove 72 of the piston rod 70. Due to the this mutual engagement of the gliding portion and the groove 72 of the piston rod 70, the dose limiting member 60 is rotatably fixed to the piston rod 70. In other words the dose limiting member 60 is splined to the piston rod 70 or is keyed engaged with the piston rod 70.

The dose limiting member 60 further comprises an external thread 63 at its outer circumference to engage with a correspondingly shaped internal thread 59 of the drive sleeve 50. In this way, the dose limiting member 60 is displaced axially with respect to the piston rod 70 as well as with respect to the drive sleeve 50 when the drive sleeve 50 rotates relative to the piston rod 70, in particular during a dose setting procedure.

During such a dose dispensing procedure, the drive sleeve 50 rotates in an opposite direction and hence the dose limiting member 70 experiences an oppositely directed axial displacement relative to the piston rod 70 and relative to the drive sleeve 50.

Typically, during a dose setting procedure, the dose limiting member 60 is displaced in proximal direction 2 towards the clutch 40. During a dose dispensing procedure, the dose limiting member 60 is displaced in the opposite direction, hence in distal direction 1 towards the drive member 80.

At its proximal end the dose limiting member 60 comprises a proximal stop portion extending from a proximal end face of the dose limiting member 60 in axial, hence proximal direction 2.

The proximal stop portion is adapted to abut with a correspondingly shaped and correspondingly oriented radially extending stop provided at a distal end of the clutch 40. By means of the mutual abutment of the proximal stop portion of the dose limiting member 60 with the stop located at the distal end of the clutch 40, a further rotation of the drive member 50 as well as of the clutch 40 relative to the piston rod 70 can be effectively inhibited.

Since the proximal stop portion of the dose limiting member 60 abuts in radial and circumferential direction with the clutch 40, any further rotation of the clutch 40 and hence any further rotation of the drive sleeve 50 rotatably coupled therewith is effectively blocked. Moreover, the clutch 40 may also provide a proximal stop for the dose limiting member 60. Due to the threaded engagement of the dose limiting member 60 and the drive sleeve 50, also here, a further rotation of the drive sleeve 50 exceeding a predefined maximum single dose configuration can be prevented. In this way, the dose limiting member 60 serves to provide a single dose limiting mechanism which is operable to effectively inhibit setting of a dose exceeding a predefined maximum single dose, e.g. 120 IU of insulin.

The dose limiting member 60 also comprises a distal stop portion extending accordingly in distal direction 1 from a distal end face of the dose limiting member 60. Here, the distal stop portion may accordingly engage with a radially inwardly and axially extending stop of the drive sleeve 50.

The position and orientation of the distal stop portion and the stop is selected such, that a mutual abutment of distal stop portion and stop is correlated with a zero dose configuration at the end of a dose dispensing procedure, i.e. when the dose indicating sleeve 100 has returned into its initial position.

Since the rotation of the drive sleeve 50 can be blocked and interrupted by the dose limiting member 60 in both directions, i.e. in a dose setting mode as well as in a dose dispensing mode, further stop features to inhibit a dose incrementing or dose decrementing rotation of the drive sleeve 50 are generally not required. As a consequence, even the dose indicating sleeve 100 and its arrangement in the body 20 can be provided without any further rotation limiting means.

The distal stop portion of the dose limiting member 60 may be further equipped with a clicking member which is adapted to generate an audible sound before or when the distal stop portion engages with the corresponding stop of the drive sleeve 50. The clicking member typically comprises a resilient arm extending in circumferential direction from the distal stop portion. At its free end the arm comprises a latch portion featuring a tooth-like shape with a slanted or tilted leading surface. During a dose dispensing procedure and well before reaching the distal stop configuration, the latch portion engages with the stop and becomes subject to a axially, hence proximally directed evasive movement due to the resilient deformability of the arm.

In a final stop configuration the latch portion may relax and may snap into a recess provided at the inside wall of the drive sleeve 50, thereby generating an audible click sound. The returning of the latch portion and the resilient arm into its initial unbiased configuration may occur before the distal stop portion engages with the stop or it may coincide with the stop configuration, thereby audibly indicating to a user, that the dose dispensing procedure is close to end or has just terminated. Said audible feedback is not only obtained at the end of a dose dispensing procedure but also when a zero dose size, e.g. 0 IU is set by means of a dose correction procedure.

A last dose sleeve 110 as illustrated in FIGS. 7 to 9 comprises an outer thread 119 extending between a distal flange 111 and a proximal flange 113. The last dose sleeve 110 is further engaged, in particular threadedly engaged with a last dose member 120, which is of annular or arc-shape as illustrated in FIGS. 7 to 9. The last dose member 120 comprises an internal thread 128 to threadedly engage with the outer thread 119 of the last dose sleeve 110 and further comprises a radially outwardly extending protrusion 122 engaged with an axially extending groove 27 provided on the inside facing sidewall of the proximal receptacle 23 of the body 20.

The groove 27 is also illustrated in the cross section A-A in FIG. 3. Since the protrusion 122 of the last dose member 120 engages with the groove 27 of the body 20, the last dose member 120 is rotatably locked to the body 20 and is therefore hindered to rotate with respect to the body 20 in circumferential direction. Due to its threaded engagement with the outer thread 119 of the last dose sleeve 110, the last dose member 120 is displaced in axial direction 1 when the last dose sleeve 110 is rotated with respect to the body 20.

Typically, the last dose member 120 comprises a leading edge and a trailing edge in circumferential direction with respect to the sense of rotation relative to the last dose member 120. By means of its leading and/or trailing edges the last dose member 120 is engageable with radially extending or radially protruding stop portions provided on the outer circumference of the last dose sleeve 110 adjacent to its proximal and distal flanges 113, 111, respectively, when reaching a last dose limiting configuration.

When the leading or trailing edge of the last dose member 120 abuts or engages with the at least one stop of the last dose sleeve 110, further rotation of the last dose sleeve 110 can be effectively blocked and inhibited, thereby blocking or inhibiting a further dose incrementing rotation of the actuation member 30 during a dose setting procedure. The radially extending leading or trailing edges of the last dose member 120 and the correspondingly shaped stops of the last dose sleeve 110 are adapted to immediately block a further rotation of the last dose sleeve 110 and hence of the actuation member 30 when a predetermined rotational position of the last dose sleeve 110 and the actuation member 30 has been reached.

The thread 119 and the axial dimensions of the last dose sleeve 110 are selected such, that an axial position of the last dose member 120 on the last dose sleeve 110 is directly correlated to the axial position of the piston rod 70 and hence to the axial position of the piston 16 in the cartridge 14.

It is to be mentioned here, that the last dose limiting mechanism implemented by the last dose sleeve 110 is beneficial in that the last dose sleeve 110 is directly located inside the actuation member 30. In effect, a tolerance chain between the actuation member 30 and the last dose limiting mechanism is fairly short and can therefore be reduced to a minimum.

Moreover, the flexibility of the various parts, of which the drive mechanism 3 is assembled may play a subordinate role, as the flux of force from the actuation member 30 to the last dose sleeve 110 is comparatively short. Moreover, also from a user's point of view, the position of the last dose sleeve 110 together with the last dose member 120 inside the actuation member 30 will provide a rather solid, robust and therefore very reliable last dose limiting mechanism.

In the embodiment as illustrated in FIG. 1 the body comprises a substantially tubular shaped body 20 that is closed in proximal direction by a closure member 130 fixedly attached to the proximal end of the housing's body 20. The closure member 130 comprises a cup-shaped cylindrical sidewall portion 132 featuring a radially inwardly extending fastening member 133 to engage with a correspondingly shaped recess of the proximal body 20. Alternatively the closure member 130 and the body 20 may also be integrally formed as a single piece and may form a proximal body 20.

Figure 10:
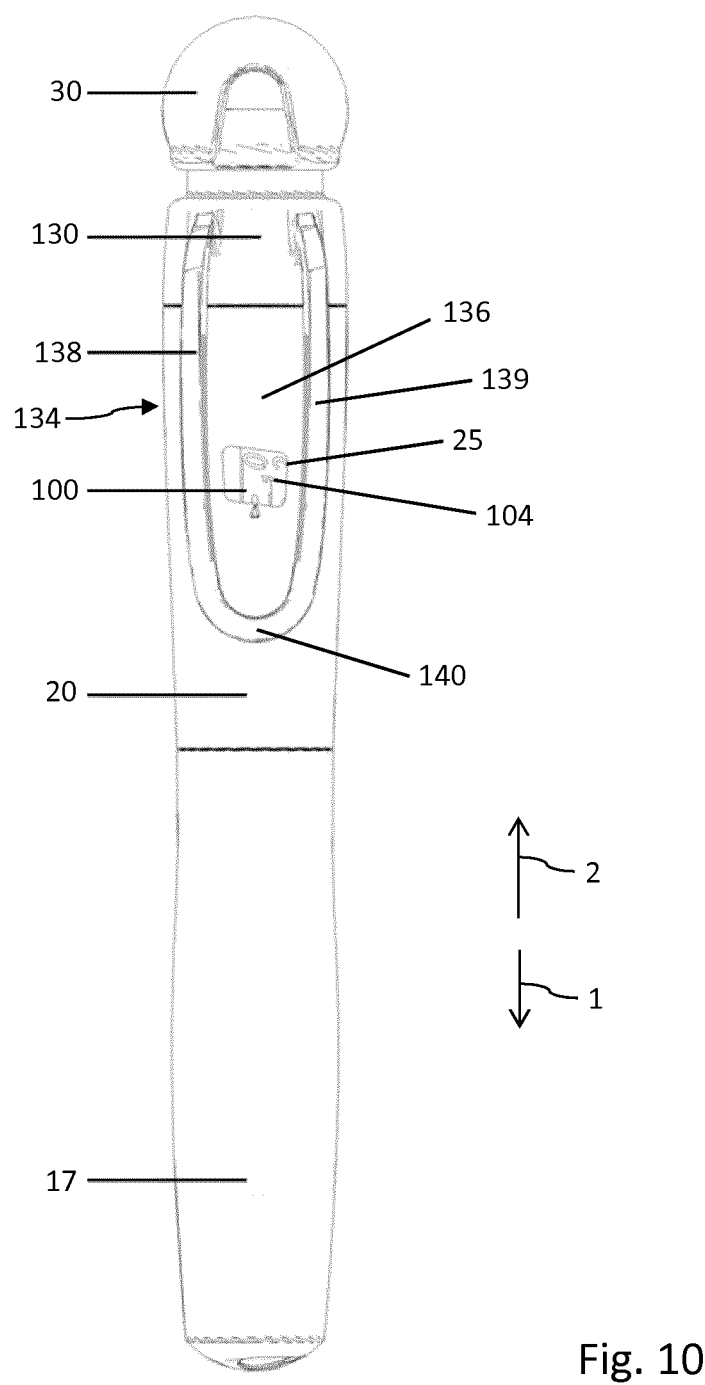

As becomes apparent from FIG. 10, the proximal body 20 is further provided with a fastening member 134 that in the present embodiment is designed as a fixing clip. Said fixing clip or fastening member 134 is integrally formed with the closure member 130 and extends from the proximal end of the body 20 in distal direction 1. Apparently the fastening member 134 is arranged at the outer surface of the housing's body 20 and extends adjacent to the dose indicating window 25. Moreover, the fastening member 134 comprises a recess 136 substantially overlapping with the dose indicating window 25 of the body 20. In this way the dose indicating numbers 104 showing up in the dose indicating window 25 are discernible through the fastening member 134.

In the embodiment as illustrated in FIG. 10 the fastening member 134 comprises two circumferentially separated but substantially parallel extending branches 138, 139 that mutually merge via a distal connecting section 140 forming a bridging portion between the two branches 138, 139. In this way the fastening member 134 comprises a U-shape and forms a recess 136 between the lateral branches 138, 139.

Alternatively it is also conceivable, that the fastening member 134 is made of a single fixing clip-like branch extending across the dose indicating window 25 but featuring a transparent section overlapping with the dose indicating window 25.

By means of the fastening member 134 arranged in an overlapping configuration with the dose indicating window 25, the dose indicating window 25 can be protected against environmental influences, such like mechanical impact. Moreover, the fastening member 134 radially outwardly extending along the proximal body 20 provides a kind of roll-away protection, e.g. when the tubular shaped drug delivery device 10 is for instance positioned on a table. The radially outwardly extending fastening member 134 effectively prevents unlimited rolling motion of the body 20 and therefore provides an additional security feature for the drug delivery device.

Moreover, and in contrast to embodiments, where a fastening member is provided on the protective cap 17 the fastening member 134 according to the embodiment of FIG. 10 allows for a direct fastening of the body 20 to e.g. a piece of cloth or to a pocket of a user. Even in the event that the protective cap 17 would inadvertently release from the body 20, the body 20 and hence almost the entire drug delivery device 10 would remain fastened to the respective piece of cloth.

It is to be noted that the fastening member 134 is universally applicable with a variety of different drug delivery devices 10 and drive mechanisms 3 that feature at least a dose indicating window 25 in a body 20.

Figures 11, 12:
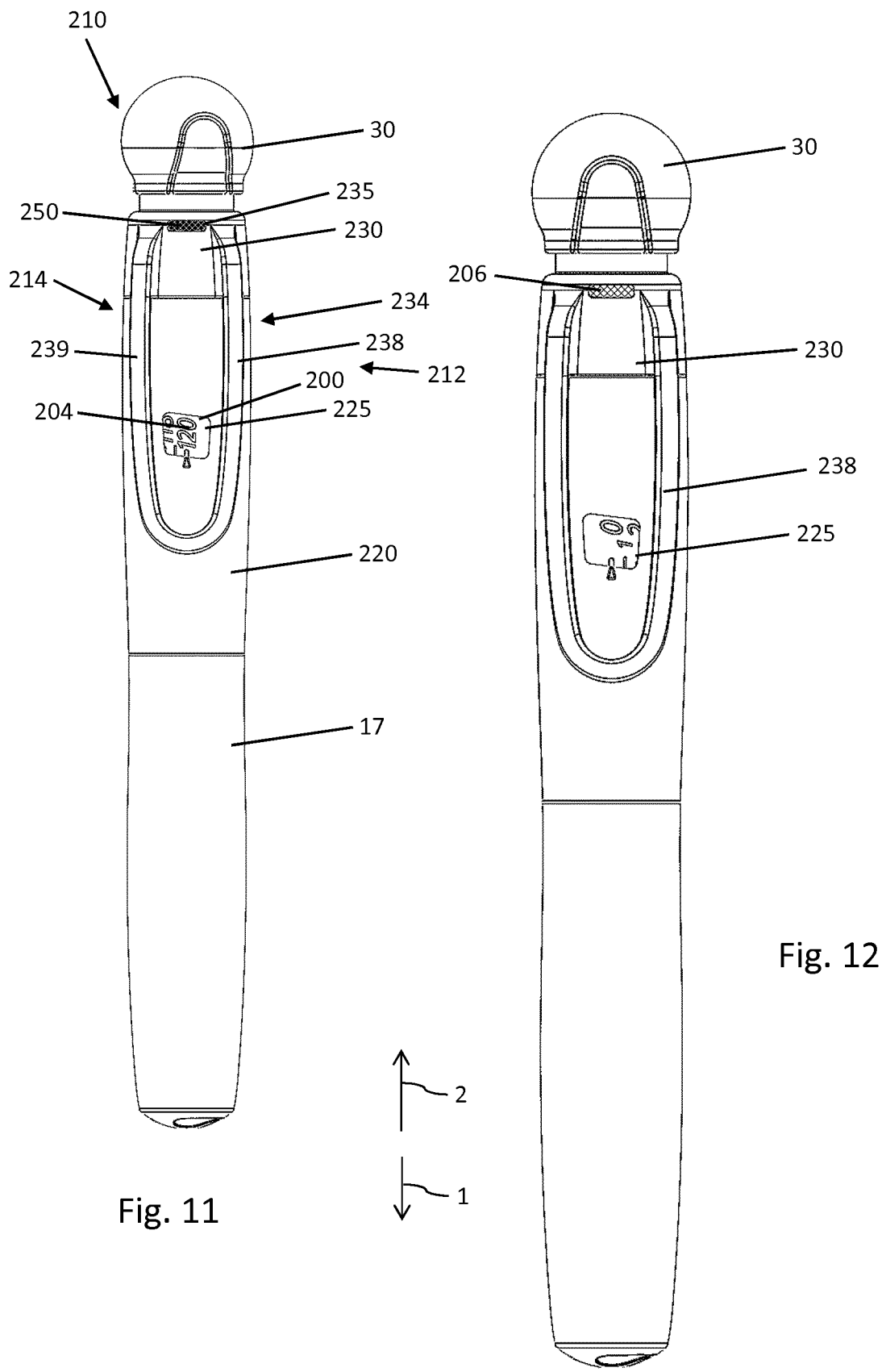
FIG. 11 illustrates another drug delivery device featuring a dose indicating mechanism with a dose indicating sleeve and with an additional indicator in a maximum dose configuration.
FIG. 12 shows the device according to FIG. 11 with the dose indicating mechanism and the drive mechanism in standby mode.

The drug delivery device 210 as illustrated in FIGS. 11-17 is fairly similar to the device 10 as illustrated and described in FIGS. 1-10. In contrast to the device 10 as illustrated in FIG. 1, the dose indicating sleeve 200 of the device 210 of FIG. 11 is in a proximal end configuration as illustrated in FIG. 12 before a dose of the medicament is to be set. Apart from that, the dose indicating sleeve 200 is threadedly engaged with a body 220 of the drug delivery device 210, wherein said body 220 has an inner thread similar or identical to the thread 28 of body 20.

Figure 15:
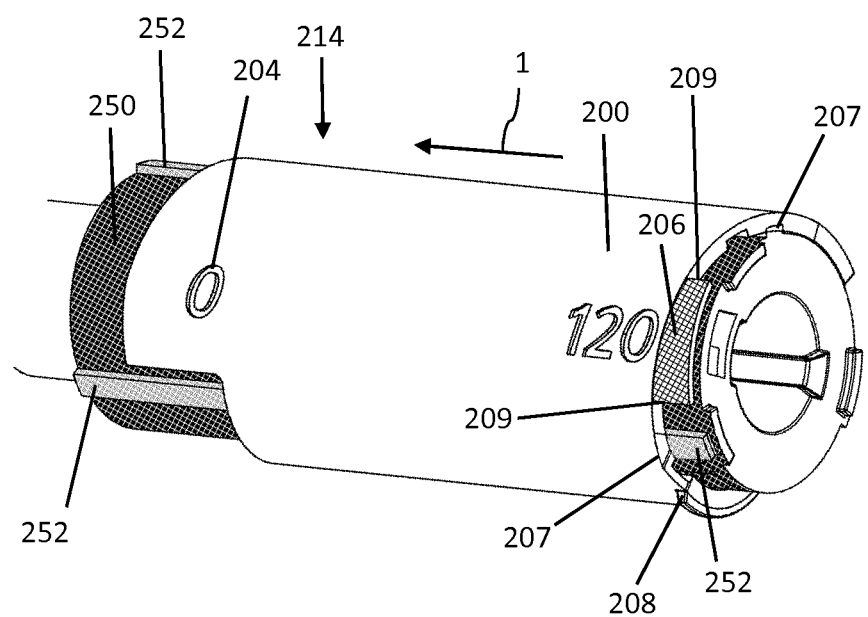
Figure 16:
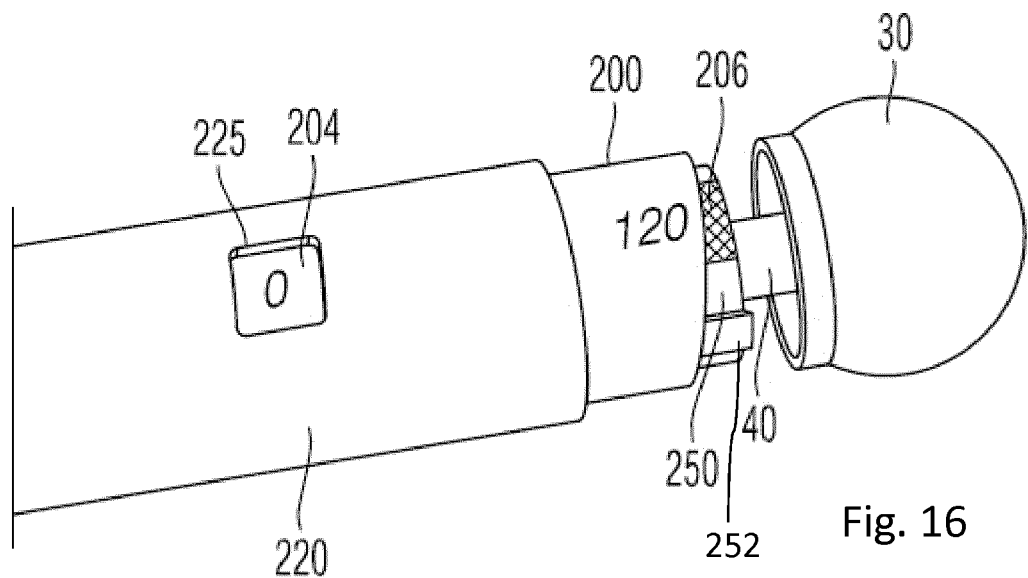
FIG. 16 shows a perspective and partially exploded view of the device in the configuration according to FIG. 12
Figure 17:
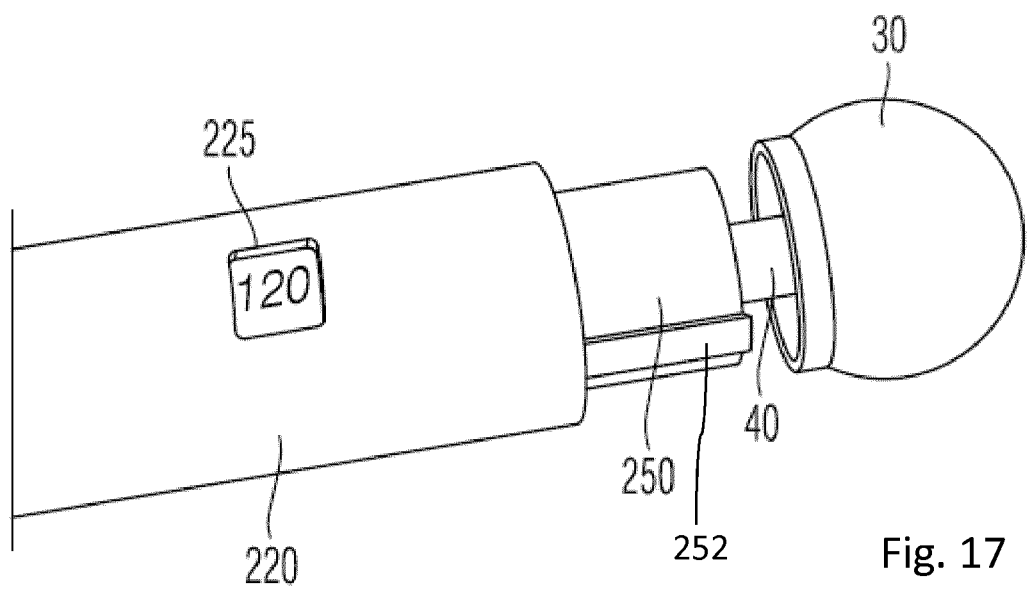
FIG. 17 shows a perspective and partially exploded view of the device in the configuration according to FIG. 11.

The dose indicating sleeve 200 as illustrated in FIG. 15 comprises a thread portion 208 at its proximal end by way of which the dose indicating sleeve 200 is threadedly engaged with the body 220. As shown in FIG. 15, the thread portion 208 comprises only one radially outwardly extending rim only partially enclosing the outer circumference of the dose indicating sleeve 200. The drive sleeve 250 as illustrated in FIG. 15 may be substantially identical to the drive sleeve 50 as shown in the embodiment according to FIG. 1.

As shown in FIG. 15, the drive sleeve 250 comprises three equidistantly arranged and axially extending protrusions 252 that engage with correspondingly-shaped axially extending recesses 207 or grooves provided at an inward facing sidewall portion of the tubular-shaped dose indicating sleeve 200. In this way, the dose indicating sleeve 200 may axially slide along the drive sleeve 250 while it is rotatably engaged with the drive sleeve 250. Hence, the dose indicating sleeve 200 is permanently rotatably coupled with the drive sleeve 250.

As the drive sleeve 250 rotates in dose incrementing direction 5, the dose indicating sleeve 200 also rotates in the dose incrementing direction 5. Due to the threaded engagement of dose indicating sleeve 200 and body 220, the dose indicating sleeve 200 experiences a distally-directed displacement, hence a displacement in distal direction 1 as the drive sleeve 250 and hence the dose indicating sleeve 200 is rotated in dose incrementing direction 5 relative to the body 220.

Figures 13, 14:
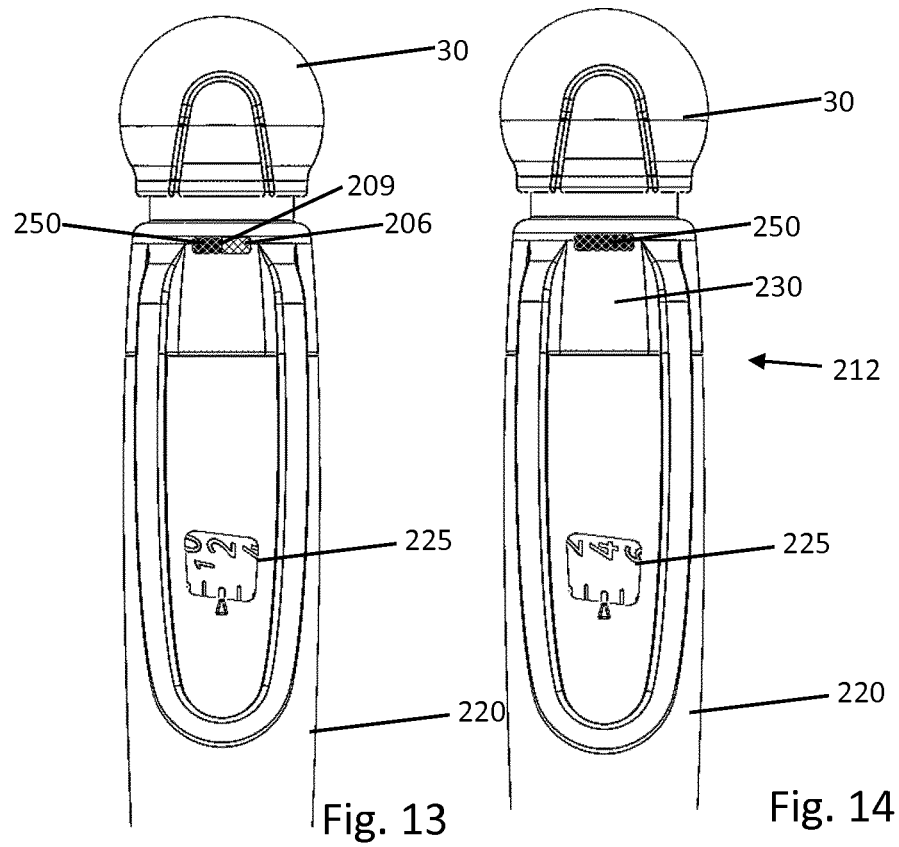
FIG. 13 shows the device according to FIGS. 11 and 12 in a configuration while priming of the device and FIG. 14 shows the device according to FIGS. 11-13 after dialing of a dose of respective size, FIG. 15 schematically shows isolated components of the dose indicating mechanism of the device according to FIGS. 11-14 in a perspective view.

As shown in the sequence of FIGS. 12, 13 and 14, consecutive numbers of the dose indication 204 located on the outer circumference of the dose indicating sleeve 200 show up in the first window 225 of the body 220. Additionally, the housing 212 of the drug delivery device 210 comprises a closure member 230 to seal or to close the proximal end of the body 220. Hence, the housing 212 of the drug delivery device 210 comprises two components, namely a tubular-shaped body 220, acting as a main housing and a closure member 230 to close the body 220 in proximal direction 2.

As illustrated in FIGS. 11-14, the housing 212 comprises a second window 235 which is located in the closure member 230. In a zero dose configuration or in standby mode of the device 210, said second window 235 axially coincides with an indicator 206 that is integrally formed with the dose indicating sleeve 200 as illustrated in FIG. 15. The indicator 206 axially protrudes from the proximal end of the dose indicating sleeve 200 and coincides with the second window 235 when the dose indicating sleeve is in its zero dose configuration, i.e. when a zero dose indicating number shows up in the first window 225 as illustrated in FIG. 12.

The indicator 206 differs in colour or in some other visually discernible feature from the dose indicating sleeve 200 and/or from the drive sleeve 250 located underneath. Moreover, the wing-shaped indicator 206 comprises at least one lateral but axially extending edge 209. Since the indicator 206 is integrally formed with the dose indicating sleeve 200 it experiences a threaded or helical motion relative to the body 220 as the dose indicating sleeve 200 is rotated, e.g. in dose incrementing direction 5.

When the actuating member 30 has been dialled for priming or for dose incrementing by an angle that represents a typical priming dose size, of e.g. 2 IU, the respective dose size shows up in the first window 225 as shown in FIG. 13. Additionally, the indicator 206 is only partially discernible in the second window 235. The lateral edge 209 then axially intersects the second window 235 in axial direction so that the drive sleeve 250 located underneath becomes discernible in the second window 235 as the dose indicating sleeve 200 is dialled in dose incrementing direction 5.

As a consequence, in configurations, wherein a dose exceeding a priming dose size has been set or dialled the indicator 206 will shift or travel beyond and outside the second window 235. The drive sleeve 250, at least a proximal portion thereof that coincides with the second window 235 then shows up in the second window 235 as long as the drive mechanism is in a non-zero dose configuration and hence no longer in a standby mode that would allow for a subsequent dose setting and dispensing.

In order to clearly and ambiguously visualize this particular operational status of the dose indicating mechanism 214, or of the drug delivery device 210 it may be of particular benefit, when the drive sleeve 250 features a luminescent or fluorescent paint at least at its proximal end section. Also the indicator 206 may feature a luminescent or fluorescent colour that clearly differs from the colour of the drive sleeve 250. For instance, the indicator 206 may be green whereas the drive sleeve 250 or at least a proximal portion thereof may be red coloured.

In the present embodiment the indicator 206 is in close vicinity and directly adjacent to a maximum dose indication '120'. In a maximum dose configuration as for instance illustrated in FIGS. 11 and 17, the indicator 206 is located in direct vicinity to the first window 225 but does not show up in said window 225 due to the single dose limiting mechanism of the drive mechanism as explained above.

Again and as already described above also the drug delivery device according to FIGS. 11-17 comprises a clip-like fastening member 234 featuring two substantially parallel branches 238, 239 by way of which the entire drug delivery device 210 can be releasably attached to e.g. a piece of cloth.

The invention claimed is:

1. A dose indicating mechanism for displaying a dose of a medicament to be dispensed by a drug delivery device, the dose indicating mechanism comprising:
   an elongated housing extending in an axial direction and having at least a first window and a second window that are spaced apart from each other in the axial direction;
   a dose indicating sleeve movably disposed in the elongated housing and having at least one dose indication coinciding with the first window to display a size of the dose actually set; and
   an indicator operably engaged with the dose indicating sleeve and axially displaceable relative to the elongated housing to coincide with the second window for indicating an operational status of the dose indicating mechanism,
   wherein the indicator is located at an axial end of the dose indicating sleeve, and wherein the indicator axially protrudes from the dose indicating sleeve,
   wherein the indicator comprises at least one axially extending lateral edge, and
   wherein the indicator is displaceable outside the second window to reveal a drive sleeve located underneath the second window.

2. The dose indicating mechanism according to claim 1, wherein the dose indicating sleeve is rotatable relative to the elongated housing.

3. The dose indicating mechanism according to claim 1, wherein the dose indicating sleeve is threadedly engaged with the elongated housing.

4. The dose indicating mechanism according to claim 1, wherein the dose indicating sleeve and the indicator are integrally formed.

5. The dose indicating mechanism according to claim 1, wherein the indicator is flush with an outer circumference of the dose indicating sleeve.

6. The dose indicating mechanism according to claim 1, wherein the elongated housing comprises a tubular shaped body and a closure member arranged at a proximal end of the tubular shaped body.

7. The dose indicating mechanism according to claim 6, wherein the first window is located in the tubular shaped body and wherein the second window is located in at least one of the tubular shaped body or the closure member.

8. The dose indicating mechanism according to claim 1, wherein the indicator comprises or forms an axial appendix of the dose indicating sleeve.

9. The dose indicating mechanism according to claim 1, wherein the at least one axially extending lateral edge extends parallel to the axial direction.

10. The dose indicating mechanism according to claim 1, wherein the at least one axially extending lateral edge is configured to axially intersect the second window in the axial direction.

11. A drug delivery device comprising:
an elongated housing extending in an axial direction and having at least a first window and a second window that are spaced apart from each other in the axial direction;
a cartridge holder to accommodate a cartridge filled with a medicament;
a dose indicating mechanism comprising
a dose indicating sleeve movably disposed in the elongated housing and having at least one dose indication coinciding with the first window to display a size of a dose actually set, and
an indicator operably engaged with the dose indicating sleeve and axially displaceable relative to the elongated housing to coincide with the second window for indicating an operational status of the dose indicating mechanism, wherein the indicator is located at an axial end of the dose indicating sleeve, and wherein the indicator axially protrudes from the dose indicating sleeve;
a piston rod to operably engage with a piston of the cartridge to displace the piston in a distal directions; and
a drive sleeve switchable between a dose setting mode and a dose dispensing mode,
wherein in the dose setting mode, the drive sleeve is operably disengaged from the piston rod and is rotatable relative to the elongated housing in a dose incrementing direction, and
wherein in the dose dispensing mode, the drive sleeve is operably engaged with the piston rod for driving the piston rod in the distal direction, and wherein the drive sleeve is rotatable relative to the elongated housing in a dose decrementing direction opposite to the dose incrementing direction.

12. The drug delivery device according to claim 11, wherein the drive sleeve comprises at least one radially extending protrusion configured to engage with a correspondingly shaped radial recess of the dose indicating sleeve.

13. The drug delivery device according to claim 11, further comprising the cartridge filled with the medicament.

14. The drug delivery device according to claim 11, wherein the indicator comprises or forms an axial appendix of the dose indicating sleeve.

15. The drug delivery device according to claim 11, wherein the indicator comprises at least one axially extending lateral edge, wherein the at least one axially extending lateral edge extends parallel to the axial direction.

16. A dose indicating mechanism for displaying a dose of a medicament to be dispensed by a drug delivery device, the dose indicating mechanism comprising:
an elongated housing extending in an axial direction and having at least a first window and a second window that are spaced apart from each other in the axial direction;
a dose indicating sleeve movably disposed in the elongated housing and having at least one dose indication coinciding with the first window to display a size of the dose actually set; and
an indicator operably engaged with the dose indicating sleeve and axially displaceable relative to the elongated housing to coincide with the second window for indicating an operational status of the dose indicating mechanism,
wherein the indicator is located at an axial end of the dose indicating sleeve, and wherein the indicator axially protrudes from the dose indicating sleeve, and
wherein the indicator is displaceable outside the second window to reveal a drive sleeve located underneath the second window.

* * * * *